(12) United States Patent
Bae et al.

(10) Patent No.: US 10,270,038 B2
(45) Date of Patent: Apr. 23, 2019

(54) FULLERENE DERIVATIVE, ORGANIC SOLAR CELL USING SAME, AND PREPARATION METHOD THEREFOR

(71) Applicant: LG CHEM, LTD., Seoul (KR)

(72) Inventors: Jaesoon Bae, Daejeon (KR); Jaechol Lee, Daejeon (KR); Jiyoung Lee, Daejeon (KR); Songrim Jang, Daejeon (KR); Keun Cho, Daejeon (KR); Doo Whan Choi, Daejeon (KR); Jiwon Bang, Daejeon (KR)

(73) Assignee: LG Chem, Ltd. (KR)

( * ) Notice: Subject to any disclaimer, the term of this patent is extended or adjusted under 35 U.S.C. 154(b) by 243 days.

(21) Appl. No.: 15/112,056

(22) PCT Filed: Feb. 5, 2015

(86) PCT No.: PCT/KR2015/001180
§ 371 (c)(1),
(2) Date: Jul. 15, 2016

(87) PCT Pub. No.: WO2015/119436
PCT Pub. Date: Aug. 13, 2015

(65) Prior Publication Data
US 2016/0329499 A1 Nov. 10, 2016

(30) Foreign Application Priority Data
Feb. 5, 2014 (KR) .................. 10-2014-0013168

(51) Int. Cl.
*H01L 51/00* (2006.01)
*C01B 32/152* (2017.01)
(Continued)

(52) U.S. Cl.
CPC ........ *H01L 51/0047* (2013.01); *C01B 32/152* (2017.08); *C07D 311/96* (2013.01); *C07D 335/04* (2013.01); *C07D 405/10* (2013.01); *C07D 407/10* (2013.01); *C07D 409/14* (2013.01); *C07D 495/10* (2013.01);
(Continued)

(58) Field of Classification Search
CPC ............. H01L 51/0046; H01L 51/0047; C01B 32/152; C07D 311/96; C07D 335/04; C07D 405/10; C07D 407/10; C07D 409/14; C07D 495/10
See application file for complete search history.

(56) References Cited

U.S. PATENT DOCUMENTS 5,739,376 A 4/1998 Bingel

FOREIGN PATENT DOCUMENTS

| JP | 2011155034 A | 8/2011 |
|----|---|---|
| JP | 2011210952 A | 10/2011 |

(Continued)

OTHER PUBLICATIONS

Li et al. "Why is the Rearrangement of [6,5] Open Fulleroids to [6,6] Closed Fullerenes Zero Order?" J. Am. Chem. Soc. 1997, 119, 1149-1150 (Year: 1997).*

(Continued)

*Primary Examiner* — Susan D Leong
(74) *Attorney, Agent, or Firm* — Myers Bigel, P.A.

(57) ABSTRACT

The present disclosure relates to a fullerene derivative, an organic solar cell including the same, and a fabrication method thereof.

21 Claims, 1 Drawing Sheet

(51) Int. Cl.
  *C07D 311/96* (2006.01)
  *C07D 335/04* (2006.01)
  *C07D 405/10* (2006.01)
  *C07D 407/10* (2006.01)
  *C07D 409/14* (2006.01)
  *C07D 495/10* (2006.01)
  *H01L 51/42* (2006.01)

(52) U.S. Cl.
  CPC ......... *H01L 51/4253* (2013.01); *Y02E 10/549* (2013.01); *Y02P 70/521* (2015.11)

(56) References Cited

FOREIGN PATENT DOCUMENTS

| KR | 10-2008-0109318 A | 12/2008 |
| KR | 10-2013-0027284 A | 3/2013 |
| KR | 10-2013-0113210 A | 10/2013 |

OTHER PUBLICATIONS

Tang: "Two-layer organic photovoltaic cell", Applied Physics Letters, vol. 48, No. 2, Jan. 13, 1986, pp. 183-185.

Yu, et a.: "Polymer Photovoltaic Cells: Enhanced Efficiencies via a Network of Internal Donor-Acceptor Heterojunctions", Science, vol. 270, Dec. 15, 1995, pp. 1789-1791.

Roncali: "Linear p-conjugated systems derivatized with C60-fullerene as molecular heterojunctions for organic photovoltaics", Chemical Society Reviews, vol. 34, 2005, pp. 483-495.

Brites, et al.: "Synthesis and fluorescence properties of [60] and [70]fullerene-coumarin dyads: Efficient dipole-dipole resonance energy transfer from coumarin to fullerene", New Journal of Chemistry, vol. 30, 2006, pp. 1036-1045.

\* cited by examiner

FULLERENE DERIVATIVE, ORGANIC SOLAR CELL USING SAME, AND PREPARATION METHOD THEREFOR

TECHNICAL FIELD

This application is a National Stage Entry of International Application No. PCT/KR2015/001180, filed Feb. 5, 2015, and claims the benefit of and priority to Korean Application No. 10-2014-0013168, filed Feb. 4, 2014, both of which are incorporated herein by reference in their entirety for all purposes as if fully set forth herein.

The present disclosure relates to fullerene derivatives, an organic solar cell using the same, and a fabricating method thereof.

BACKGROUND ART

A solar cell using an organic material has been highlighted due to the advantages of easy processability, diversity, low fabricating costs, and high flexibility, and is rapidly growing along with the development of a new material.

An organic semiconductor has been forecast to emerge as an essential material in the fabrication of an inexpensive solar cell, such as a thin film-type device, a large area device, and a flexible device which may be applied by a roll-to-roll method, based on low costs and easiness in fabrication process, which are the largest advantages of an organic material.

The possibility of an organic solar cell was first proposed in the 1970s, but the efficiency thereof was so low that no practical use was found.

However, in 1986, C. W. Tang at Eastman Kodak Company showed the possibility of commercialization into various solar cells from a two-layer structure using copper phthalocyanine (CuPc) and a perylene tetracarboxylic acid derivative, and as a result, great development has been brought while interests in and researches for the organic solar cell have been rapidly increased.

Thereafter, as a concept of bulk heterojunction (BHJ) was introduced by Yu, et al., in 1995, and a fullerene derivative with enhanced solubility, such as PCBM was developed as an n-type semiconductor material, a breakthrough has been achieved in terms of efficiency of the organic solar cell.

However, problems in that a starting material fullerene is expensive and difficult to synthesize, the solubility thereof is not good, and the like are still a big obstacle to the development of an e-donor material.

In order to replace the existing material, studies have been continuously conducted on the development of e-donor materials having low bandgap and new e-acceptor materials having good charge mobility.

CITATION LIST

Non-Patent Document

Two-layer organic photovoltaic cell (C. W. Tang, Appl. Phys. Lett., 48, 183. (1996))

Efficiencies via Network of Internal Donor-Acceptor Heterojunctions (G. Yu, J. Gao, J. C. Hummelen, F. Wudl, A. J. Heeger, Science, 270, 1789. (1995))

DISCLOSURE

Technical Problem

An object of the present disclosure is to provide fullerene derivatives having thermal stability, high solubility and electron mobility, an organic solar cell including the same, and a fabricating method thereof.

Technical Solution

In an exemplary embodiment of the present disclosure, provided is a fullerene derivative represented by the following Formula 1.

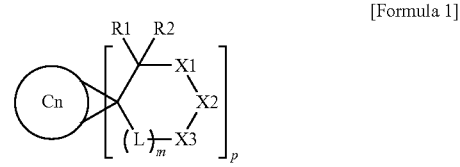

[Formula 1]

In Formula 1,

Cn is a $C_{60}$ to $C_{84}$ fullerene, p is an integer of 1 to 4, the structures in the parenthesis are the same as or different from each other when p is 2 or more, L is CRaRb, m is an integer of 0 to 3, Ls are the same as or different from each other when m is 2 or more, X1 to X3 are the same as or different from each other, and are each independently S; O; PR; CRR'; $SO_2$; P(=O)R; or SiRR', at least one of X1 to X3 is S; O; PR; $SO_2$; P(=O)R; or SiRR', R1, R2, Ra, Rb, R and R' are the same as or different from each other, and are each independently hydrogen; deuterium; a halogen group; a nitrile group; a nitro group; an imide group; an amide group; a hydroxyl group; an ester group; a carbonyl group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, or two substituents adjacent to each other in R1, R2, Ra, Rb, R and R' combine with each other to form a double bond; cycloalkyl; cycloalkenyl; cycloketone; an aromatic ring; or a hetero ring, or two substituents in the same atom in R1, R2, Ra, Rb, R and R' combine with each other to form a spiro bond; a carbonyl group; an immine group; or an alkenyl group, the formed cycloalkyl, cycloalkenyl, aromatic ring; hetero ring, or spiro bond is unsubstituted or substituted with an additional substituent, when X1 and X3 are the same as or different from each other, and are each independently PR, CRR', P(=O)R, or SiRR', and m is 1, R1 or R2 and R or R' of X1; and Ra or Rb and R or R' of X3 do not form an aromatic ring simultaneously, and when X2 is S, m is 1, R1 and R2 are hydrogen, or Ra and Rb are hydrogen, and two substituents adjacent to each other in R1, R2, Ra, Rb, R and R' combine with each other to form an aromatic ring, the aromatic ring is substituted with an additional substituent.

The present disclosure provides an organic solar cell including: a first electrode; a second electrode provided to face the first electrode; and an organic material layer including one or more layers provided between the first electrode and the second electrode and including a photoactive layer, in which one or more layers of the organic material layer includes the above-described fullerene derivative.

Further, the present disclosure provides a method for fabricating an organic solar cell, the method including: preparing a substrate; forming a first electrode on an upper portion of the substrate; forming an organic material layer including one or more layers, which includes a photoactive layer on an upper portion of the first electrode; and forming a second electrode on an upper portion of the organic material layer, in which the organic material layer including one or more layers includes the above-described fullerene derivative.

Advantageous Effects

A fullerene derivative according to an exemplary embodiment of the present disclosure may be used as a material for an organic material layer of not only an organic solar cell including the fullerene derivative, but also an organic electron device.

Not only an organic solar cell including the fullerene derivative according to an exemplary embodiment of the present disclosure, but also an organic electron device exhibit an increase in efficiency and/or an increase in stability.

The fullerene derivative according to an exemplary embodiment of the present disclosure may be used either alone or in mixture with impurities in an organic solar cell, and may be applied by vacuum deposition or a solution application method, and the like.

The fullerene derivative according to an exemplary embodiment of the present disclosure enhances light efficiency and is excellent in thermal stability, thereby enhancing life characteristics of a device.

EXPLANATION OF REFERENCE NUMERALS AND SYMBOLS

Figure 1:
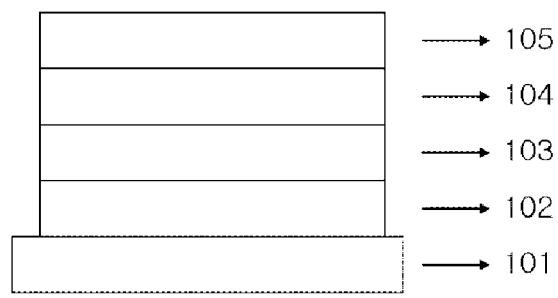
FIG. 1 illustrates an organic solar cell according to an exemplary embodiment.
Figure 2:
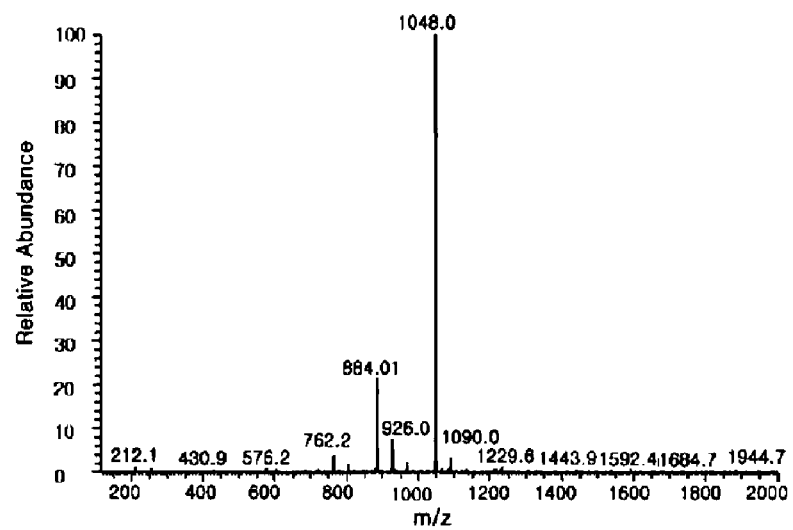
FIG. 2 is a view illustrating the MS spectrum of Formula 1-1-1.

101: Substrate
102: First electrode
103: Hole transport layer
104: Photoactive layer
105: Second electrode

BEST MODE

Hereinafter, the present disclosure will be described in detail.

In an exemplary embodiment of the present disclosure, provided is the fullerene derivative represented by Formula 1.

In an exemplary embodiment of the present disclosure, two substituents adjacent to each other in R1, R2, Ra, Rb, R and R' may combine with each other to form cycloalkyl; cycloalkenyl; cyclic ketone; an aromatic ring; or a hetero ring.

In an exemplary embodiment of the present disclosure, two substituents adjacent to each other in R1, R2, Ra, Rb, R and R' may combine with each other to form an aromatic ring or a hetero ring.

When adjacent substituents combine with each other to form an aromatic ring or a hetero ring, the charge mobility may be increased due to the n-n interaction between aromatic rings and molecule in the e-donor material.

The adjacent substituent in the present disclosure means a substituent substituted with the adjacent carbon.

In the present disclosure, the adjacent group and cycloalkyl, cycloalkenyl, cyclic ketone, an aromatic ring, and a hetero ring may each form a 5-membered to 6-membered ring, and may be monocyclic or polycyclic.

In an exemplary embodiment of the present disclosure, X1 is CRR', and R or R' combines with R1 or R2 to form an aromatic ring.

In this case, X2 and/or X3 are/is S; O; PR; $SO_2$; P(=O)R; or SiRR'.

In an exemplary embodiment of the present disclosure, X2 is CRR', X3 is CRR', and R or R' of X2 combines with R or R' of X3 to form an aromatic ring.

In this case, X1 is S; O; PR; $SO_2$; P(=O)R; or SiRR'.

Examples of the substituents will be described below, but are not limited thereto.

The term "substituted or unsubstituted" as used herein means being substituted with one or more substituents selected from the group consisting of deuterium; a halogen group; an alkyl group; an alkenyl group; an alkoxy group; an ester group; a carbonyl group; a carboxyl group; a hydroxyl group; a cycloalkyl group; a silyl group; an arylalkenyl group; an aryloxy group; an alkylthioxy group; an alkylsulfoxy group; an arylsulfoxy group; a boron group; an alkylamine group; an aralkylamine group; an arylamine group; a heteroaryl group; a carbazole group; an arylamine group; an aryl group; a fluorenyl group; a nitrile group; a nitro group; a hydroxyl group; and a heterocyclic group, or having no substituent. The substituent may be substituted with a substituent to which two or more substituents are linked in the exemplified substituents, and for example, "the substituent to which two or more substituents are linked" may be a biphenyl group. That is, the biphenyl group may also be an aryl group, and may be interpreted as a substituent to which two phenyl groups are linked.

The substituents may be unsubstituted or substituted with an additional substituent.

In the present disclosure, a halogen group may be fluorine, chlorine, bromine or iodine.

In the present disclosure, the imide group may be represented by

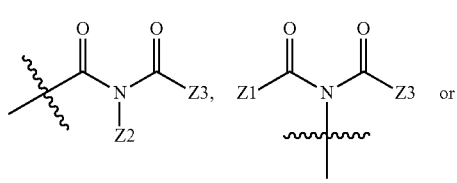

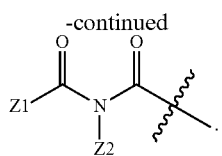

Z1 to Z3 are the same as or different from each other, and hydrogen; a substituted or unsubstituted straight, branched, or cyclic alkyl group having 1 to 25 carbon atoms; or a substituted or unsubstituted aryl group having 6 to 25 carbon atoms. Specifically, Z1 to Z3 are the same as or different from each other, and a substituted or unsubstituted straight, branched, or cyclic alkyl group having 6 to 25 carbon atoms; or a substituted or unsubstituted aryl group having 6 to 25 carbon atoms.

In the present disclosure, the amide group may be represented by

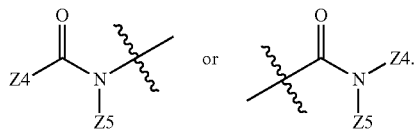

Z4 and Z5 are the same as or different from each other, and are each independently hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted heterocyclic group having 2 to 60 carbon atoms.

In the present disclosure, the general formula of the ester group may be represented by

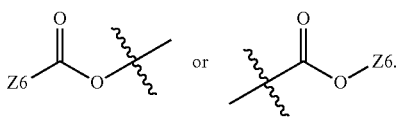

Z6 is hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted heterocyclic group having 2 to 60 carbon atoms.

In the present disclosure, the carbonyl group may be represented by

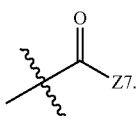

Z7 is hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted heterocyclic group having 2 to 60 carbon atoms.

In the present disclosure, the imine group may be represented by

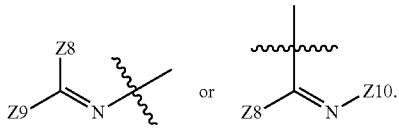

Z8 to Z10 are the same as or different from each other, and hydrogen; a substituted or unsubstituted straight, branched, or cyclic alkyl group having 1 to 25 carbon atoms; or a substituted or unsubstituted aryl group having 6 to 25 carbon atoms. Specifically, Z8 to Z10 are the same as or different from each other, and a substituted or unsubstituted straight, branched, or cyclic alkyl group having 6 to 25 carbon atoms; or a substituted or unsubstituted aryl group having 6 to 25 carbon atoms.

In the present disclosure, the ether group may be represented by

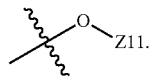

Z11 is hydrogen; a substituted or unsubstituted straight, branched, or cyclic alkyl group having 1 to 25 carbon atoms; or a substituted or unsubstituted aryl group having 6 to 25 carbon atoms. Specifically, Z11 is the same as or different from each other, and a substituted or unsubstituted straight, branched, or cyclic alkyl group having 6 to 25 carbon atoms; or a substituted or unsubstituted aryl group having 6 to 25 carbon atoms.

In an exemplary embodiment of the present disclosure, the ether group is an alkyl ether group.

In the present disclosure, the alkyl group may be straight or branched, and the number of carbon atoms thereof is not particularly limited, but is preferably 1 to 60.

Specifically, the alkyl group is preferably an alkyl group having 6 to 60 carbon atoms.

Specific examples thereof include a methyl group, an ethyl group, a propyl group, a butyl group, a pentyl group, a hexyl group, a heptyl group, an octyl group, a nonanyl group, a decanyl group, an undecanyl group, a dodecanyl group, an icosanyl group, and the like, or a branched chain thereof, but are not limited thereto, and the alkyl groups may be substituted with an additional substituent.

In the present disclosure, the cycloalkyl group is not particularly limited, but has preferably 3 to 60 carbon atoms, and specifically, has 5 to 60 carbon atoms.

Specific examples thereof include cyclopropyl, cyclobutyl, cyclopentyl, cyclohexyl, cycloheptyl, cyclooctyl, a norbornyl group, an adamantly group, and the like, but are not limited thereto, and the alkoxy groups may be substituted with an additional substituent.

In the present disclosure, the cyclo in the cycloalkoxy may be selected from the above-described examples of the cycloalkyl group.

In the present disclosure, the alkoxy group may be straight, branched, or cyclic. The number of carbon atoms of the alkoxy group is not particularly limited, but is preferably 1 to 60. More specifically, the alkoxy group is preferably an alkoxy group having 10 to 60 carbon atoms.

Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, 2-ethylhexyloxy, 2-methylheptyloxy, 2-propylbutyloxy, n-octyloxy, n-nonyloxy, n-decyloxy, benzyloxy, p-methylbenzyloxy, and the like, but are not limited thereto, and the alkoxy groups may be substituted with an additional substituent.

In the present disclosure, the arylalkyl group is not particularly limited in the number of carbon atoms, but in an exemplary embodiment of the present disclosure, the number of carbon atoms of the arylalkyl group is 7 to 50. Specifically, the number of carbon atoms of the aryl moiety is 6 to 49, and the number of carbon atoms of the alkyl moiety is 1 to 44. Specific examples thereof include a phenyl methyl group, a phenyl ethyl group, a phenyl propyl group, a phenyl isopropyl group, a phenyl butyl group, a phenyl isobutyl group, a phenyl pentyl group, a phenyl isopentyl group, a phenyl hexyl group, a phenyl isohexyl group, a phenyl heptyl group, a phenyl octyl group, a phenyl nonanyl group, a phenyl decanyl group, a naphthyl methyl group, a naphthyl ethyl group, a naphthyl propyl group, a naphthyl isopropyl group, a pyrenyl methyl group, a pyrenyl ethyl group, a pyrenyl propyl group, a pyrenyl isopropyl group, a pyrrolyl methyl group, a pyrrolyl ethyl group, a thiophenylmethyl group, a thiophenylethyl group, a thiophenylpropyl group, a thiophenylisopropyl group, a thiophenylbutyl group, and the like, but are not limited thereto, and the arylalkyl groups may be substituted with an additional substituent.

In the present disclosure, the arylalkyl in the arylalkyloxy group may be selected from the above-described examples of the arylalkyl group.

In the present disclosure, the alkenyl group may be straight or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, stilbenyl, styrenyl, and the like, but are not limited thereto, and the alkenyl groups may be substituted with an additional substituent.

In the present disclosure, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto, and the silyl groups may be substituted with an additional substituent.

In the present disclosure, the aryl group may be monocyclic, and the number of carbon atoms is not particularly limited, but is preferably 6 to 60. Specific examples of the aryl group include a monocyclic aromatic group, such as a phenyl group, a biphenyl group, a triphenyl group, a terphenyl group, and a stilbene group, a polycyclic aromatic group, such as a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group, and the like, but are not limited thereto, and these aryl groups may be substituted with an additional substituent.

Further, in the present disclosure, the aromatic ring may be selected from the examples of the aryl group.

In the present disclosure, the fluorenyl group includes the structure of an open fluorenyl group, and herein, the open fluorenyl group has a structure in which the linkage of one ring compound is broken in the structure in which two ring organic compounds are linked through one atom.

When the fluorenyl group is substituted, the fluorenyl group may be

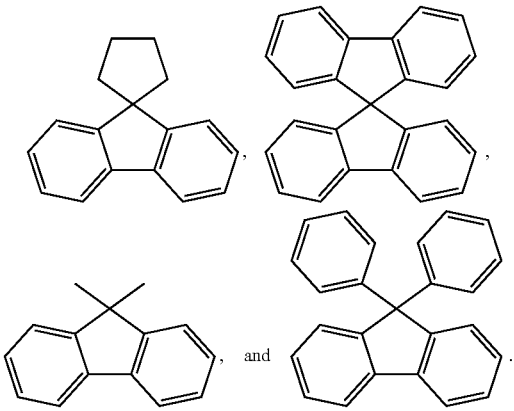

However, the fluorenyl group is not limited thereto, and may be substituted with an additional substituent.

In the present disclosure, a heterocyclic group or a heteroaryl group is a hetero atom, for example, a heterocyclic group including one or more of O, N, S, Si, Se and the like, and the number of carbon atoms is not particularly limited, but is preferably 2 to 60. Examples of the heterocyclic group include a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a qinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a dibenzofuranyl group, and the like, but are not limited thereto, and the heteroaryl group may be substituted with an additional substituent.

In the present disclosure, the heteroaryl in the heteroaryloxy group may be selected from the above-described examples of the heteroaryl group.

In the present disclosure, the aryl group in the aryloxy group, the arylthioxy group, the arylsulfoxy group, and the aralkylamine group is the same as the above-described examples of the aryl group.

In the present disclosure, the alkyl group in the alkylthioxy group, the alkylsulfoxy group, the alkylamine group, and the aralkylamine group is the same as the above-described examples of the alkyl group. Specific examples thereof include a methylthioxy group, an ethylthioxy group, a propylthioxy group, a butylthioxy group, a pentylthioxy group, a hexylthioxy group, a heptylthioxy group, an octylthioxy group, a nonanylthioxy group, a decylthioxy group, and the like, specific examples of the alkylsulfoxy group include a methylsulfoxy group, an ethylsulfoxy group, a propylsulfoxy group, a butylsulfoxy group, a pentylsulfoxy group, a hexylsulfoxy group, a heptylsulfoxy group, an octylsulfoxy group, a nonanyl group, a decylsulfoxy group, and the like, and these groups may also be a branched chain, and are not limited thereto. The alkyl groups may be substituted with an additional substituent.

In the present disclosure, the number of carbon atoms of the alkylamine group is not particularly limited, but is preferably 1 to 60. Specifically, the number of carbon atoms of the alkylamine group is preferably 3 to 50. Specific examples of the amine group include a methylamine group, an ethylamine group, a propylamine group, a butylamine group, a pentylamine group, a hexylamine group, a heptylamine group, an octylamine group, a nonanylamine group, a decylamine group, and the like, these groups may also be a branched chain, but are not limited thereto, and the alkyl groups may be substituted with an additional substituent.

In the present disclosure, examples of the arylamine group include a substituted or unsubstituted monoarylamine group and a substituted or unsubstituted diarylamine group. The aryl group in the arylamine group may be a monocyclic aryl group or a polycyclic aryl group. Two or more arylamine groups which the aryl group includes may include a monocyclic aryl group, a polycyclic aryl group, or both a monocyclic aryl group and a polycyclic aryl group.

For the aryl group of the arylamine group, specifically, one or more are selected from the group consisting of a phenyl group, a naphthyl group, a biphenyl group, an anthracenyl group, a pyrenyl group, a fluorenyl group, a tetracenyl group, a chrysenyl group, a fluorenyl group, an acenaphthacenyl group, a triphenylene group, and a fluoranthene group, and the arylamine group may be substituted with an additional substituent.

In the present disclosure, for the heteroaryl group in the heteroarylamine group, one or more are selected from the group consisting of a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a qinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, and a dibenzofuran group in the above-described examples of the heterocyclic group, and the heteroaryl group may be substituted with an additional substituent.

In the present disclosure,

means a site bonded to another substituent or a binding portion.

In an exemplary embodiment of the present disclosure, a substituent in the same atom means a substituent sharing one atom, and for example, a substituent corresponding to R1 and R2 in Formula 1 is a substituent in the same atom.

In an exemplary embodiment of the present disclosure, the substituent in the same carbon forms a double bond. Examples thereof include a carbonyl group; and a substituted or unsubstituted imine group, and are not limited thereto.

In the present disclosure, the substituent in the same carbon forms a spiro bond. The spiro bond means a structure in which two ring organic compounds are linked to each other through one atom. In addition, the spiro bond may include a structure in which the linkage of one ring compound is broken in the structure of two ring organic compounds linked through one atom.

The structure formed by the spiro bond may be a hydrocarbon ring or a hetero ring including one or more of N, O, and S atoms. The hydrocarbon ring may be an aliphatic ring or an aromatic ring, and The hetero ring may be an aliphatic hetero ring or an aromatic hetero ring.

In the present disclosure, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups "adjacent" to each other.

The hydrocarbon ring or the hetero ring may be a monocycle or a polycycle.

In the present disclosure, a cycloalkyl, a cycloalkenyl, and an aromatic ring; and a hetero ring or a spiro bond formed by binding two or more substituents are unsubstituted or substituted with an additional substituent.

The additional substituent is deuterium; a halogen group; a nitrile group; a nitro group; an imide group; an amide group; a hydroxyl group; an ester group; a carbonyl group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, or may mean a double bond; cycloalkyl; cycloalkenyl; cycloketone; an aromatic ring; or a hetero ring by combining the two substituents adjacent to each other, and are the same as those described above.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In an exemplary embodiment of the present disclosure, R1, R2, Ra, Rb, R and R' are the same as or different from each other, and are each independently hydrogen; a halogen group; an ester group; a substituted or unsubstituted alkyl group; a substituted or unsubstituted arylamine group; a substituted or unsubstituted alkoxy group; or a substituted or unsubstituted aryl group, or two substituents adjacent to each other in R1, R2, Ra, Rb, R and R' combine with each other to form a double bond; an aromatic ring; or a hetero ring, or two substituents in the same atom in R1, R2, Ra, Rb, R and R' combine with each other to form a spiro bond; or a carbonyl group, and the formed aromatic ring; hetero ring or spiro bond is unsubstituted or substituted with a halogen group; a substituted or unsubstituted alkoxy group; a substituted or unsubstituted alkyl group; or a substituted or unsubstituted arylamine group.

In an exemplary embodiment of the present disclosure, m is an integer of 0 to 3.

In an exemplary embodiment of the present disclosure, m is 1.

In an exemplary embodiment of the present disclosure, the structure in [ ] in Formula 1 is represented by any one of the following Formulae 2 to 13.

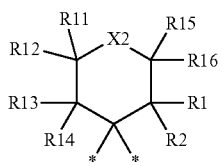
[Formula 2]

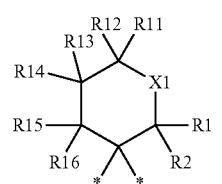
[Formula 3]

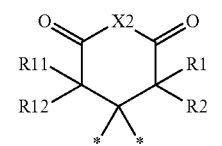
[Formula 4]

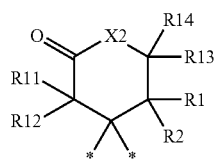
[Formula 5]

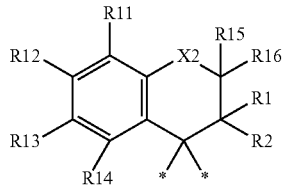
[Formula 6]

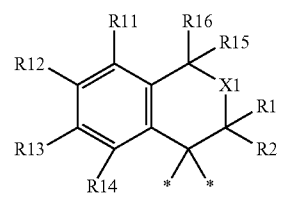
[Formula 7]

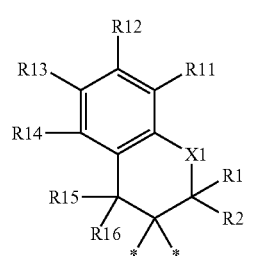
[Formula 8]

-continued

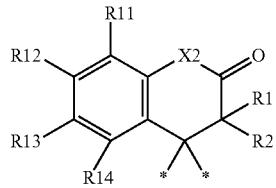
[Formula 9]

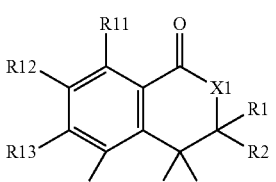
[Formula 10]

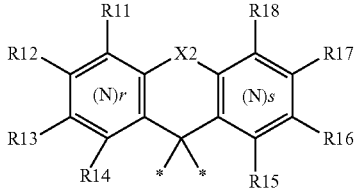
[Formula 11]

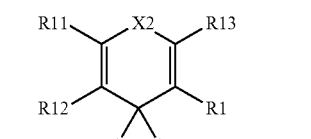
[Formula 12]

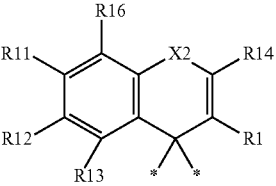
[Formula 13]

In Formulae 2 to 13,

X1, X2, R1 and R2 are the same as those defined in Formula 1, (N)s and (N)r mean those substituted with a nitrogen atom instead of carbon in a benzene ring, and s and r are each an integer of 0 to 4, s+r≥1, 11 to R16 are the same as or different from each other, and are each independently hydrogen; deuterium; a halogen group; a nitrile group; a nitro group; an imide group; an amide group; a hydroxyl group; an ester group; a carbonyl group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; or a substituted or unsubstituted heterocyclic group, or two substituents adjacent to each other in R11 to R16 combine with each other to form a double bond; cycloalkyl; cycloalkenyl; cyclic ketone; an aromatic ring; or a hetero ring, or two substituents in the same atom in R11 to R16 combine with each other to form a spiro bond; a carbonyl group; an imine group; or an alkenyl group, and the formed cycloalkyl; cycloalkenyl; cyclic ketone; aromatic ring; or hetero ring or spiro bond is unsubstituted or substituted with an additional substituent.

In an exemplary embodiment of the present disclosure, R11 to R16 are the same as or different from each other, and are each independently hydrogen; a halogen group; a carbonyl group; a substituted or unsubstituted alkyl group; a substituted or unsubstituted alkoxy group; a substituted or unsubstituted arylamine group; a substituted or unsubstituted aryl group, or two substituents adjacent to each other in R11 to R16 combine with each other to form an aromatic ring; or a hetero ring, or two substituents in the same atom combine with each other to form a spiro bond, and the formed aromatic ring; hetero ring; or spiro bond is unsubstituted or substituted with an additional substituent.

The additional substituent is the same as those described above.

In an exemplary embodiment of the present disclosure, L is CRaRb.

In another exemplary embodiment, Ra is hydrogen.

In still another exemplary embodiment, Rb is hydrogen.

In an exemplary embodiment of the present disclosure, Ra is a halogen group.

In an exemplary embodiment of the present disclosure, Ra is chlorine.

In an exemplary embodiment of the present disclosure, Ra is fluorine.

In an exemplary embodiment of the present disclosure, Ra is a substituted or unsubstituted alkyl group.

In another exemplary embodiment, Ra is a substituted or unsubstituted methyl group.

In still another exemplary embodiment, Ra is a methyl group.

In an exemplary embodiment of the present disclosure, Ra is a substituted or unsubstituted ester group.

In another exemplary embodiment, Ra is an ester group substituted with an ethyl group.

In an exemplary embodiment of the present disclosure, Rb is a halogen group.

In an exemplary embodiment of the present disclosure, Rb is chlorine.

In an exemplary embodiment of the present disclosure, Rb is fluorine.

In an exemplary embodiment of the present disclosure, Rb is a substituted or unsubstituted alkyl group.

In another exemplary embodiment, Rb is a substituted or unsubstituted methyl group.

In still another exemplary embodiment, Rb is a methyl group.

In an exemplary embodiment of the present disclosure, Rb is a substituted or unsubstituted ester group.

In another exemplary embodiment, Rb is an ester group substituted with an ethyl group.

In one exemplary embodiment, Ra and Rb combine with each other to form a substituted or unsubstituted spiro bond.

In an exemplary embodiment of the present disclosure, Ra and Rb combine with each other to form cyclohexane as a spiro bond.

In another exemplary embodiment, Ra and Rb combine with each other to form piperidine as a spiro bond.

In an exemplary embodiment of the present disclosure, X3 is CRR'

In an exemplary embodiment of the present disclosure, Ra or Rb and R or R' combine with each other to form a substituted or unsubstituted aromatic ring.

Ra or Rb and R or R' combine with each other to form a substituted or unsubstituted hetero ring.

Ra or Rb and R or R' combine with each other to form a six-membered hetero ring including N.

Ra or Rb and R or R' combine with each other to form a double bond.

In the present disclosure, the double bond means that in the case of having a six-membered structure in which m in Formula 1 is 1, a double bond is included in a six-membered ring.

In an exemplary embodiment of the present disclosure, X1 of Formula 1 is O.

In an exemplary embodiment of the present disclosure, X2 of Formula 1 is O.

In an exemplary embodiment of the present disclosure, X3 of Formula 1 is O.

In an exemplary embodiment of the present disclosure, R1 is hydrogen.

In an exemplary embodiment of the present disclosure, R1 is a halogen group.

In an exemplary embodiment of the present disclosure, R1 is chlorine.

In an exemplary embodiment of the present disclosure, R1 is fluorine.

In an exemplary embodiment of the present disclosure, R1 is a substituted or unsubstituted alkyl group.

In another exemplary embodiment, R1 is a substituted or unsubstituted methyl group.

In still another exemplary embodiment, R1 is a methyl group.

In an exemplary embodiment of the present disclosure, R1 is an alkyl group substituted with an ester group.

In another exemplary embodiment, R1 is an ethyl group substituted with an ester group.

In an exemplary embodiment of the present disclosure, R1 is a substituted or unsubstituted alkenyl group.

In another exemplary embodiment, R1 is an alkenyl group substituted with a cyano group.

In an exemplary embodiment of the present disclosure, R1 is an ethenyl group substituted with a cyano group.

In an exemplary embodiment of the present disclosure, R1 is an alkenyl group substituted with an ester group.

In an exemplary embodiment of the present disclosure, R1 is an alkenyl group substituted with a cyano group and an ester group.

In another exemplary embodiment, R1 is an ethenyl group substituted with a cyano group and an ester group.

In an exemplary embodiment of the present disclosure, R1 is an alkenyl group substituted with a substituted or unsubstituted aryl group.

In another exemplary embodiment, R1 is an alkenyl group unsubstituted or substituted with a phenyl group.

In another exemplary embodiment, R1 is an alkenyl group substituted with a cyano group and a substituted or unsubstituted phenyl group.

In still another exemplary embodiment, R1 is an ethenyl group substituted with a cyano group and a substituted or unsubstituted phenyl group.

In an exemplary embodiment of the present disclosure, R1 is an alkenyl group substituted with a halogen group.

In another exemplary embodiment, R1 is an alkenyl group substituted with fluorine.

In an exemplary embodiment of the present disclosure, R1 is an alkenyl group substituted with a substituted or unsubstituted hetero ring.

In an exemplary embodiment of the present disclosure, R1 is an alkenyl group substituted with thioxothiazolidinone.

In another exemplary embodiment, R1 is an ethenyl group substituted with substituted or unsubstituted thioxothiazolidinone.

In an exemplary embodiment of the present disclosure, R1 is a substituted or unsubstituted hetero ring.

In another exemplary embodiment, R1 is a substituted or unsubstituted benzimidazole group.

In an exemplary embodiment of the present disclosure, R1 is a benzimidazole group unsubstituted or substituted with a phenyl group.

In another exemplary embodiment, R1 is a substituted or unsubstituted benzoxazole group.

In still another exemplary embodiment, R1 is a substituted or unsubstituted benzothiazole group.

In an exemplary embodiment of the present disclosure, R2 is a substituted or unsubstituted ester group.

In another exemplary embodiment, R2 is an ester group substituted with an ethyl group.

In an exemplary embodiment of the present disclosure, R2 is hydrogen.

In an exemplary embodiment of the present disclosure, R2 is a halogen group.

In an exemplary embodiment of the present disclosure, R2 is chlorine.

In an exemplary embodiment of the present disclosure, R2 is fluorine.

In an exemplary embodiment of the present disclosure, R2 is a substituted or unsubstituted alkyl group.

In another exemplary embodiment, R2 is a substituted or unsubstituted methyl group.

In still another exemplary embodiment, R2 is a methyl group.

In an exemplary embodiment of the present disclosure, R2 is a substituted or unsubstituted ester group.

In another exemplary embodiment, R2 is an ester group substituted with an ethyl group.

In an exemplary embodiment of the present disclosure, X1 is CRR'

In an exemplary embodiment of the present disclosure, R1 or R2 and R or R' combine with each other to form a substituted or unsubstituted aromatic ring.

In another exemplary embodiment of the present disclosure, R1 or R2 and R or R' combine with each other to form a substituted or unsubstituted aromatic ring.

R1 or R2 and R or R' combine with each other to form a substituted or unsubstituted hetero ring.

R1 or R2 and R or R' combine with each other to form a six-membered hetero ring including N.

R1 or R2 and R or R' combine with each other to form a double bond.

In one exemplary embodiment, an aromatic ring formed by combining the two substituents adjacent to each other is additionally substituted with a halogen group.

In another exemplary embodiment, an aromatic ring formed by combining the two substituents adjacent to each other is substituted with fluorine.

In still another exemplary embodiment, an aromatic ring formed by combining the two substituents adjacent to each other is substituted with bromine.

In yet another exemplary embodiment, an aromatic ring formed by combining the two substituents adjacent to each other is substituted with chlorine.

In still yet another exemplary embodiment, an aromatic ring formed by combining the two substituents adjacent to each other is substituted with a substituted or unsubstituted alkoxy group.

In further another exemplary embodiment, an aromatic ring formed by combining the two substituents adjacent to each other is substituted with a substituted or unsubstituted methoxy group.

In yet further another exemplary embodiment, an aromatic ring formed by combining the two substituents adjacent to each other is substituted with a methoxy group.

In still yet further another exemplary embodiment, an aromatic ring formed by combining the two substituents adjacent to each other is substituted with an ethoxy group.

In an exemplary embodiment of the present disclosure, an aromatic ring formed by combining the two substituents adjacent to each other is substituted with a substituted or unsubstituted arylamine group.

In one exemplary embodiment, an aromatic ring formed by combining the two substituents adjacent to each other is substituted with an arylamine group unsubstituted or substituted with a phenyl group.

In one exemplary embodiment, an aromatic ring formed by combining the two substituents adjacent to each other is substituted with a substituted or unsubstituted hetero ring.

In one exemplary embodiment, an aromatic ring formed by combining the two substituents adjacent to each other is substituted with a substituted or unsubstituted hetero ring including one or more S atoms.

In another exemplary embodiment, an aromatic ring formed by combining the two substituents adjacent to each other is substituted with a substituted or unsubstituted thiophene group.

In still another exemplary embodiment, an aromatic ring formed by combining the two substituents adjacent to each other is substituted with a thiophene group substituted with a thiophene group substituted with an alkyl group.

In an exemplary embodiment of the present disclosure, an aromatic ring formed by combining the two substituents adjacent to each other is a monocyclic six-membered ring.

In another exemplary embodiment, an aromatic ring formed by combining the two substituents adjacent to each other is a polycyclic six-membered ring.

In an exemplary embodiment of the present disclosure, an aromatic ring formed by combining the two substituents adjacent to each other is substituted with a substituted or unsubstituted alkyl group.

In another exemplary embodiment, an aromatic ring formed by combining the two substituents adjacent to each other is substituted with a substituted or unsubstituted methyl group.

In still another exemplary embodiment, an aromatic ring formed by combining the two substituents adjacent to each other is substituted with a methyl group.

In an exemplary embodiment of the present disclosure, X2 is CRR'.

In an exemplary embodiment of the present disclosure, R is hydrogen.

In an exemplary embodiment of the present disclosure, R is a halogen group.

In an exemplary embodiment of the present disclosure, R is chlorine.

In an exemplary embodiment of the present disclosure, R is fluorine.

In an exemplary embodiment of the present disclosure, R is a substituted or unsubstituted alkyl group.

In another exemplary embodiment, R is a substituted or unsubstituted methyl group.

In still another exemplary embodiment, R is a methyl group.

In an exemplary embodiment of the present disclosure, R is an alkyl group unsubstituted or substituted with a heterocyclic group.

In an exemplary embodiment of the present disclosure, R is an alkyl group substituted with isoindolinedione.

In an exemplary embodiment of the present disclosure, R is a methyl group substituted with isoindolinedione.

In an exemplary embodiment of the present disclosure, R is a substituted or unsubstituted aryl group.

In another exemplary embodiment, R is a substituted or unsubstituted phenyl group.

In still another exemplary embodiment, R is a phenyl group.

In an exemplary embodiment of the present disclosure, R' is hydrogen.

In an exemplary embodiment of the present disclosure, R' is a halogen group.

In an exemplary embodiment of the present disclosure, R' is chlorine.

In an exemplary embodiment of the present disclosure, R' is fluorine.

In an exemplary embodiment of the present disclosure, R' is a substituted or unsubstituted alkyl group.

In another exemplary embodiment, R' is a substituted or unsubstituted methyl group.

In still another exemplary embodiment, R' is a methyl group.

In an exemplary embodiment of the present disclosure, R' is an alkyl group unsubstituted or substituted with a heterocyclic group.

In an exemplary embodiment of the present disclosure, R' is an alkyl group substituted with isoindolinedione.

In an exemplary embodiment of the present disclosure, R' is a methyl group substituted with isoindolinedione.

In an exemplary embodiment of the present disclosure, R' is a substituted or unsubstituted aryl group.

In another exemplary embodiment, R' is a substituted or unsubstituted phenyl group.

In still another exemplary embodiment, R' is a phenyl group.

In one exemplary embodiment, R and R' combine with each other to form a substituted or unsubstituted spiro bond.

In an exemplary embodiment of the present disclosure, R and R' combine with each other to form cyclohexane as a spiro bond.

In another exemplary embodiment, R and R' combine with each other to form piperidine as a spiro bond.

In an exemplary embodiment of the present disclosure, the structure in [ ] in Formula 1 is any one of the following Formulae.

-continued

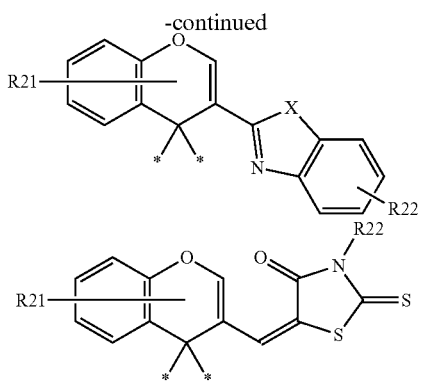

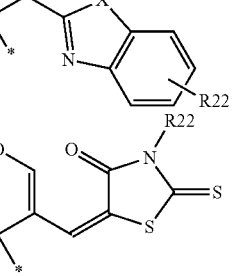

In the structure,

X is S, O or NR23,

R21 is hydrogen; a halogen group; a substituted or unsubstituted alkyl group having 1 to 60 carbon atoms; a substituted or unsubstituted alkoxy group having 1 to 60 carbon atoms; a substituted or unsubstituted amine group having 1 to 60 carbon atoms; a substituted or unsubstituted aryl group having 6 to 60 carbon atoms; or a substituted or unsubstituted heterocyclic group having 2 to 60 carbon atoms, and R22 and R23 are the same as or different from each other, and are each independently hydrogen; a substituted or unsubstituted alkyl group having 1 to 60 carbon atoms; a substituted or unsubstituted aryl group having 6 to 60 carbon atoms; or a substituted or unsubstituted heterocyclic group having 2 to 60 carbon atoms.

The structures may be substituted with an additional substituent.

R21 and R22 mean a substituent having the structure, and may be present in a plural number. When R21 and R22 are present in a plural number, a plurality of R21s or R22s is the same as or different from each other.

In an exemplary embodiment of the present disclosure, R21 may be hydrogen.

In an exemplary embodiment of the present disclosure, R21 is a substituted or unsubstituted alkyl group having 1 to 60 carbon atoms.

In an exemplary embodiment of the present disclosure, R21 is a halogen group.

In another exemplary embodiment, R21 is a substituted or unsubstituted alkoxy group having 1 to 60 carbon atoms.

In still another exemplary embodiment, R21 is a substituted or unsubstituted amine group having 1 to 60 carbon atoms.

In yet another exemplary embodiment, R21 is a substituted or unsubstituted aryl group having 6 to 60 carbon atoms.

Specifically, R21 may have the following structure.

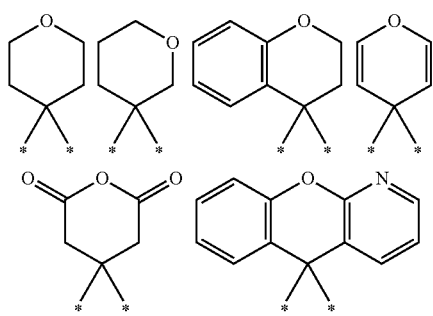

-continued

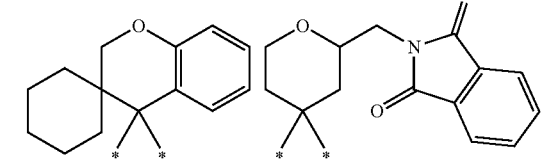

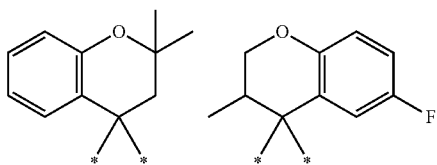

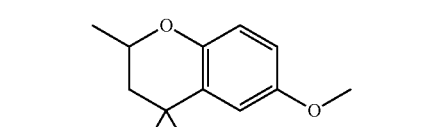

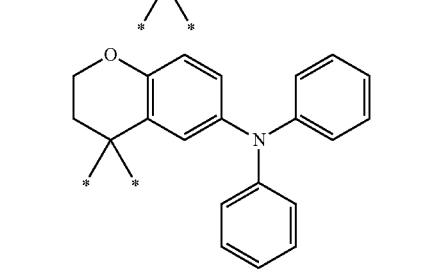

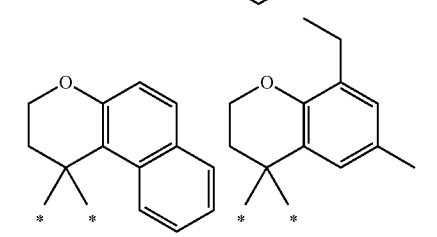

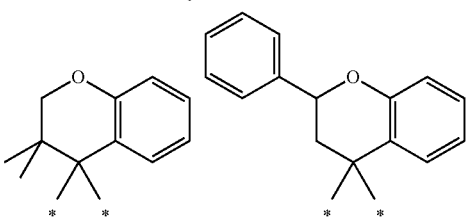

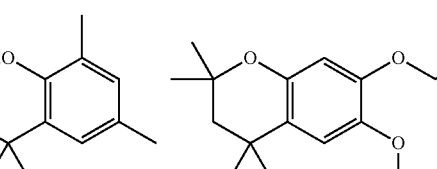

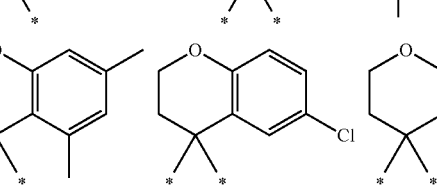

-continued

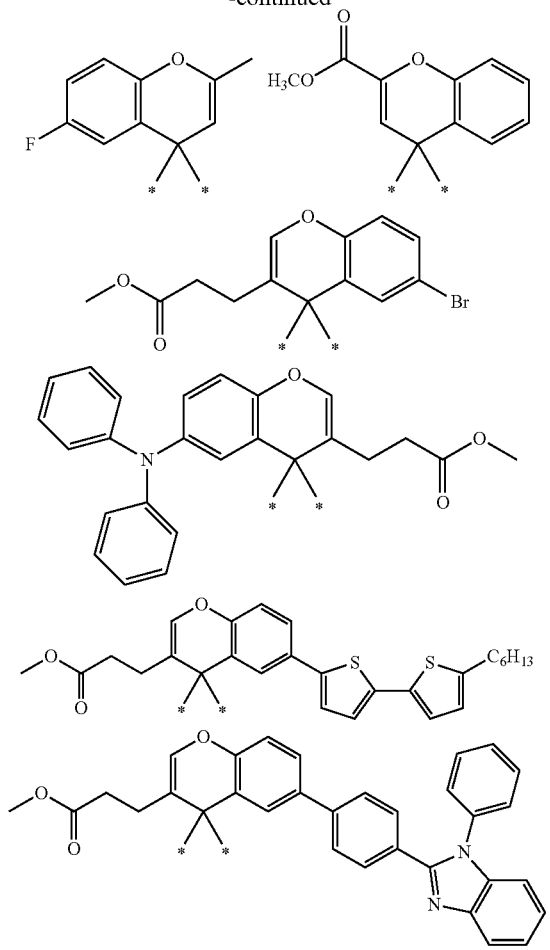

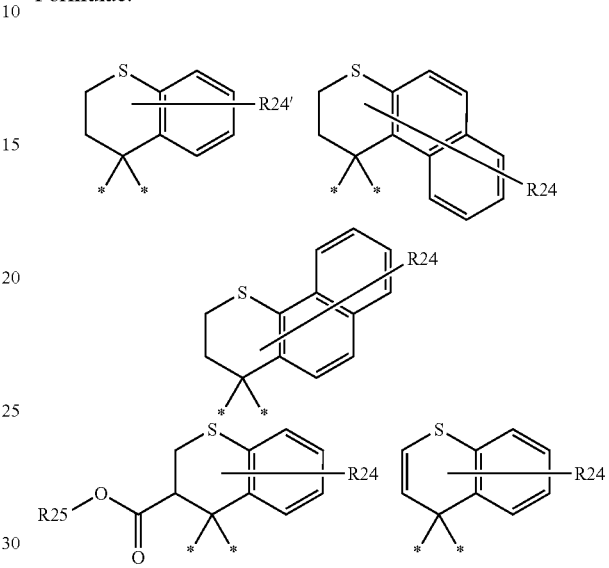

The phenyl group, the substituted thiophene group, the fluorine, the bromine or the chlorine of the hydrogen, the methyl group, the methoxy group, the ethyloxy group, the phenyl group, and the diphenylamine group, which are substituted in the structure may be changed into hydrogen; an alkyl group, such as a methyl group, an ethyl group, a propyl group, a butyl group, a pentyl group, a hexyl group, a heptyl group, an octyl group, a nonanyl group, a decanyl group, an undecanyl group, a dodecanyl group, and an icosanyl group; an alkoxy group, such as methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, 2-ethylhexyloxy, 2-methylheptyloxy, 2-propylbutyloxy, n-octyloxy, n-nonyloxy, n-decyloxy, benzyloxy, and p-methylbenzyloxy; an aryl group, such as a phenyl group, a biphenyl group, a triphenyl group, a terphenyl group, a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group; and a heterocyclic group, such as a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group and a dibenzofuranyl group, and the substituents may be substituted with an additional substituent.

In an exemplary embodiment of the present disclosure, X2 is S.

In an exemplary embodiment of the present disclosure, the structure in [ ] in Formula 1 is any one of the following Formulae.

In the structure,

R24' is a halogen group; a substituted or unsubstituted alkyl group having 1 to 60 carbon atoms; a substituted or unsubstituted alkoxy group having 1 to 60 carbon atoms; a substituted or unsubstituted amine group having 1 to 60 carbon atoms; a substituted or unsubstituted aryl group having 6 to 60 carbon atoms; or a substituted or unsubstituted heterocyclic group having 2 to 60 carbon atoms, R24 is hydrogen; a halogen group; a substituted or unsubstituted alkyl group having 1 to 60 carbon atoms; a substituted or unsubstituted alkoxy group having 1 to 60 carbon atoms; a substituted or unsubstituted amine group having 1 to 60 carbon atoms; a substituted or unsubstituted aryl group having 6 to 60 carbon atoms; or a substituted or unsubstituted heterocyclic group having 2 to 60 carbon atoms, and R25 is hydrogen; a substituted or unsubstituted alkyl group having 1 to 60 carbon atoms; an aryl group having 6 to 60 carbon atoms; or a substituted or unsubstituted heterocyclic group having 2 to 60 carbon atoms.

In an exemplary embodiment of the present disclosure, the structures may be substituted with an additional substituent.

R24', R24 and R25 mean a substituent having the structure, and may be present in a plural number. When R24', R24 and R25 are present in a plural number, a plurality of R24's, a plurality of R24s and a plurality of R25s are the same as or different from each other.

In an exemplary embodiment of the present disclosure, R24 may be hydrogen.

In an exemplary embodiment of the present disclosure, R24 is a substituted or unsubstituted alkyl group having 1 to 60 carbon atoms.

In an exemplary embodiment of the present disclosure, R24 is a halogen group.

In another exemplary embodiment, R24 is a substituted or unsubstituted alkoxy group having 1 to 60 carbon atoms.

In still another exemplary embodiment, R24 is a substituted or unsubstituted amine group having 1 to 60 carbon atoms.

In yet another exemplary embodiment, R24 is a substituted or unsubstituted aryl group having 6 to 60 carbon atoms.

In an exemplary embodiment of the present disclosure, R24' is a substituted or unsubstituted alkyl group having 1 to 60 carbon atoms.

In an exemplary embodiment of the present disclosure, R24' is a substituted or unsubstituted alkyl group having 1 to 10 carbon atoms.

In an exemplary embodiment of the present disclosure, R24' is a halogen group.

In another exemplary embodiment, R24' is a substituted or unsubstituted alkoxy group having 1 to 60 carbon atoms.

In still another exemplary embodiment, R24' is a substituted or unsubstituted alkoxy group having 1 to 10 carbon atoms.

In yet another exemplary embodiment, R24' is a substituted or unsubstituted amine group having 1 to 60 carbon atoms.

In still yet another exemplary embodiment, R24' is a substituted or unsubstituted aryl group having 6 to 60 carbon atoms.

In exemplary embodiments of the present disclosure, specifically, R24' may have the following structure.

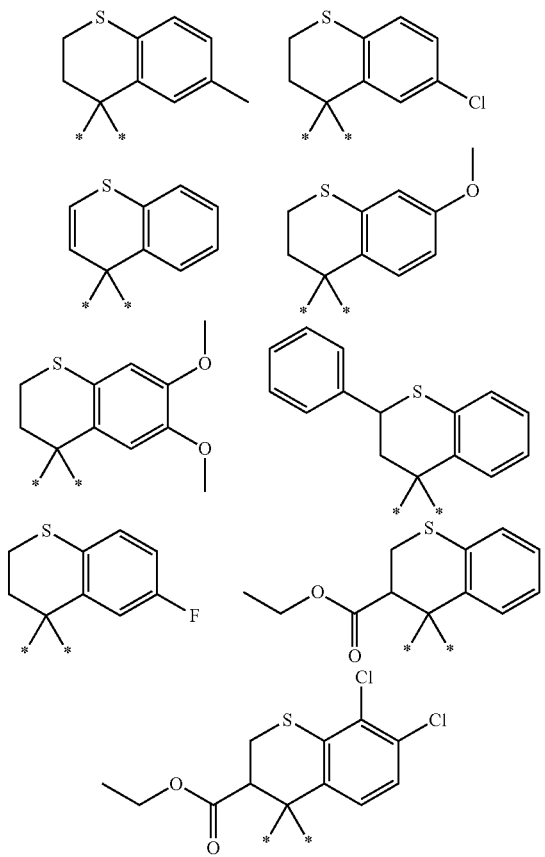

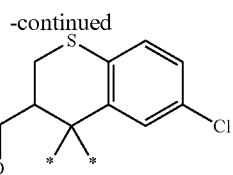

The hydrogen, the methyl group, the ethyl group, the methoxy group, or the chlorine, which is substituted in the structure may be changed into hydrogen; an alkyl group, such as a methyl group, an ethyl group, a propyl group, a butyl group, a pentyl group, a hexyl group, a heptyl group, an octyl group, a nonanyl group, a decanyl group, an undecanyl group, a dodecanyl group, and an icosanyl group; an alkoxy group, such as methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, 2-ethylhexyloxy, 2-methylheptyloxy, 2-propylbutyloxy, n-octyloxy, n-nonyloxy, n-decyloxy, benzyloxy, and p-methylbenzyloxy; an aryl group, such as a phenyl group, a biphenyl group, a triphenyl group, a terphenyl group, a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group; and a heterocyclic group, such as a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group and a dibenzofuranyl group, and the substituents may be substituted with an additional substituent.

In an exemplary embodiment of the present disclosure, X2 is SO$_2$.

In an exemplary embodiment of the present disclosure, the structure in [ ] in Formula 1 is any one of the following Formulae.

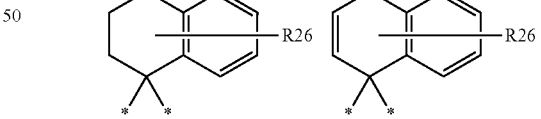

In the structure,

R26 is hydrogen; a halogen group; a substituted or unsubstituted alkyl group having 1 to 60 carbon atoms; a substituted or unsubstituted alkoxy group having 1 to 60 carbon atoms; a substituted or unsubstituted amine group having 1 to 60 carbon atoms; a substituted or unsubstituted aryl group having 6 to 60 carbon atoms; or a substituted or unsubstituted heterocyclic group having 2 to 60 carbon atoms.

In an exemplary embodiment of the present disclosure, the structures may be substituted with an additional substituent.

R26 means a substituent having the structure, and may be present in a plural number. When R26 is present in a plural number, a plurality of R26s is the same as or different from each other.

In an exemplary embodiment of the present disclosure, R26 may be hydrogen.

In an exemplary embodiment of the present disclosure, R26 is a substituted or unsubstituted alkyl group having 1 to 60 carbon atoms.

In an exemplary embodiment of the present disclosure, R26 is a halogen group.

In another exemplary embodiment, R26 is a substituted or unsubstituted alkoxy group having 1 to 60 carbon atoms.

In still another exemplary embodiment, R26 is a substituted or unsubstituted amine group having 1 to 60 carbon atoms.

In yet another exemplary embodiment, R26 is a substituted or unsubstituted aryl group having 6 to 60 carbon atoms.

Specifically, R26 may have the following structure.

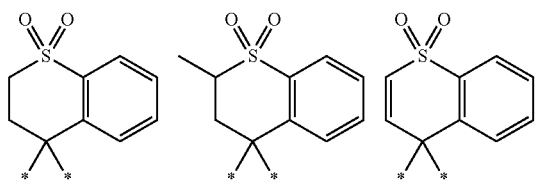

The hydrogen or the methyl group, which is substituted in the structure may be changed into hydrogen; an alkyl group, such as a methyl group, an ethyl group, a propyl group, a butyl group, a pentyl group, a hexyl group, a heptyl group, an octyl group, a nonanyl group, a decanyl group, an undecanyl group, a dodecanyl group, and an icosanyl group; an alkoxy group, such as methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, 2-ethylhexyloxy, 2-methylheptyloxy, 2-propylbutyloxy, n-octyloxy, n-nonyloxy, n-decyloxy, benzyloxy, and p-methylbenzyloxy; an aryl group, such as a phenyl group, a biphenyl group, a triphenyl group, a terphenyl group, a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group; and a heterocyclic group, such as a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group and a dibenzofuranyl group, and the substituents may be substituted with an additional substituent.

In an exemplary embodiment of the present disclosure, X2 is P(=O)R.

In an exemplary embodiment of the present disclosure, the structure in [ ] in Formula 1 is any one of the following Formulae.

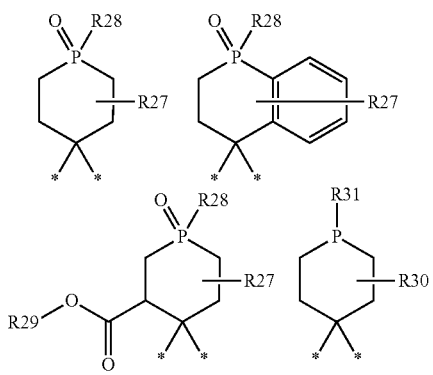

In the structure,

R27 and R30 are the same as or different from each other, and are each independently hydrogen; a halogen group; a substituted or unsubstituted alkyl group having 1 to 60 carbon atoms; a substituted or unsubstituted alkoxy group having 1 to 60 carbon atoms; a substituted or unsubstituted amine group having 1 to 60 carbon atoms; a substituted or unsubstituted aryl group having 6 to 60 carbon atoms; or a substituted or unsubstituted heterocyclic group having 2 to 60 carbon atoms, and R28, R29 and R31 are the same as or different from each other, and are each independently hydrogen; a substituted or unsubstituted alkyl group having 1 to 60 carbon atoms; a substituted or unsubstituted aryl group having 6 to 60 carbon atoms; or a substituted or unsubstituted heterocyclic group having 2 to 60 carbon atoms.

In an exemplary embodiment of the present disclosure, the structures may be substituted with an additional substituent.

R27 and R29 mean a substituent having the structure, and may be present in a plural number. When R27 is present in a plural number, a plurality of R27s is the same as or different from each other.

In an exemplary embodiment of the present disclosure, R27 may be hydrogen.

In an exemplary embodiment of the present disclosure, R27 is a substituted or unsubstituted alkyl group having 1 to 60 carbon atoms.

In an exemplary embodiment of the present disclosure, R27 is a halogen group.

In another exemplary embodiment, R27 is a substituted or unsubstituted alkoxy group having 1 to 60 carbon atoms.

In still another exemplary embodiment, R27 is a substituted or unsubstituted amine group having 1 to 60 carbon atoms.

In yet another exemplary embodiment, R27 is a substituted or unsubstituted aryl group having 6 to 60 carbon atoms.

In exemplary embodiments of the present disclosure, specifically, R27 may have the following structure.

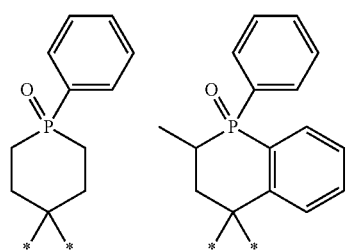

-continued

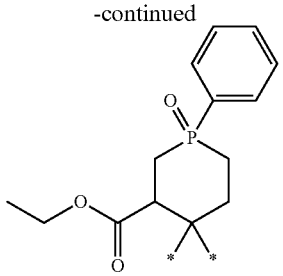

The hydrogen, the methyl group, the ethyl group, or the phenyl group, which is substituted in the structure may be changed into hydrogen; an alkyl group, such as a methyl group, an ethyl group, a propyl group, a butyl group, a pentyl group, a hexyl group, a heptyl group, an octyl group, a nonanyl group, a decanyl group, an undecanyl group, a dodecanyl group, and an icosanyl group; an alkoxy group, such as methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, 2-ethylhexyloxy, 2-methylheptyloxy, 2-propylbutyloxy, n-octyloxy, n-nonyloxy, n-decyloxy, benzyloxy, and p-methylbenzyloxy; an aryl group, such as a phenyl group, a biphenyl group, a triphenyl group, a terphenyl group, a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group; and a heterocyclic group, such as a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group and a dibenzofuranyl group, and the substituents may be substituted with an additional substituent.

In an exemplary embodiment of the present disclosure, X2 is PR.

In an exemplary embodiment of the present disclosure, the structure in [ ] in Formula 1 is any one of the following Formulae.

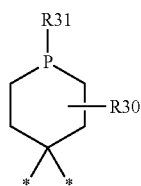

In the structure,

R30 is hydrogen; a halogen group; a substituted or unsubstituted alkyl group having 1 to 60 carbon atoms; a substituted or unsubstituted alkoxy group having 1 to 60 carbon atoms; a substituted or unsubstituted amine group having 1 to 60 carbon atoms; a substituted or unsubstituted aryl group having 6 to 60 carbon atoms; or a substituted or unsubstituted heterocyclic group having 2 to 60 carbon atoms, and R31s are the same as or different from each other, and are each independently hydrogen; a substituted or unsubstituted alkyl group having 1 to 60 carbon atoms; a substituted or unsubstituted aryl group having 6 to 60 carbon atoms; or a substituted or unsubstituted heterocyclic group having 2 to 60 carbon atoms.

In an exemplary embodiment of the present disclosure, the structures may be substituted with an additional substituent.

R30 and R31 mean a substituent having the structure, and may be present in a plural number. When R30 is present in a plural number, a plurality of R30s is the same as or different from each other.

In an exemplary embodiment of the present disclosure, R30 may be hydrogen.

In an exemplary embodiment of the present disclosure, R30 is a substituted or unsubstituted alkyl group having 1 to 60 carbon atoms.

In an exemplary embodiment of the present disclosure, R30 is a halogen group.

In another exemplary embodiment, R30 is a substituted or unsubstituted alkoxy group having 1 to 60 carbon atoms.

In still another exemplary embodiment, R30 is a substituted or unsubstituted amine group having 1 to 60 carbon atoms.

In yet another exemplary embodiment, R30 is a substituted or unsubstituted aryl group having 6 to 60 carbon atoms.

In exemplary embodiments of the present disclosure, specifically, R30 may have the following structure.

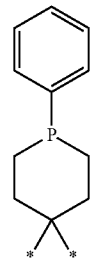 [SMILES: *C1(*)CCP(c2ccccc2)CC1]

The hydrogen or the phenyl group, which is substituted in the structure may be changed into hydrogen; an alkyl group, such as a methyl group, an ethyl group, a propyl group, a butyl group, a pentyl group, a hexyl group, a heptyl group, an octyl group, a nonanyl group, a decanyl group, an undecanyl group, a dodecanyl group, and an icosanyl group; an alkoxy group, such as methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, 2-ethylhexyloxy, 2-methylheptyloxy, 2-propylbutyloxy, n-octyloxy, n-nonyloxy, n-decyloxy, benzyloxy, and p-methylbenzyloxy; an aryl group, such as a phenyl group, a biphenyl group, a triphenyl group, a terphenyl group, a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group; and a heterocyclic group, such as a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group and a dibenzofuranyl group, and the substituents may be substituted with an additional substituent.

In the formula, * represents a site which is bonded to carbon atoms constituting a fullerene backbone of a fullerene derivative, and is not limited as long as * is a position at which carbon atoms may be bonded.

In an exemplary embodiment of the present disclosure, Cn is a structure of compounds having a pentagonal or hexagonal ring. The positions of carbons which form a pentagonal or hexagonal ring may be substituted with hydrogen or other substituents. That is, the fullerene derivative of Formula 1 may be additionally substituted with another substituent.

The fullerene derivative according to an exemplary embodiment of the present disclosure may further include another structure in addition to the structure in the parenthesis in Formula 1.

an exemplary embodiment of the present disclosure, the fullerene backbone of the fullerene derivative may be used alone, and may also be used in combination at any combination and ratio of two or more fullerene backbones.

Exemplary embodiment of the present disclosure, the fullerene derivative has a LUMO energy level of −3.4 eV to −5.0 eV.

When an electric field is applied to the fullerene derivative having a LUMO energy level in the range, the fullerene derivative has a molecular orbital in which holes and electrons are easily injected, that is, HOMO and LUMO energy levels, and thus has an effect in that injection of charges and/or mobility of current are/is enhanced.

Further, the fullerene derivative according to an exemplary embodiment of the present disclosure may have a sufficient overlapping of frontier orbitals in which charges may be effectively moved between adjacent molecules. Accordingly, an organic solar cell using the fullerene derivative may have high efficiency.

The fullerene derivative according to an exemplary embodiment of the present disclosure has excellent solubility, and thus enables a solution process at low temperature when an organic solar cell is fabricated, so that a thin film may be easily formed even on a plastic substrate, and thus the fullerene derivative is economically efficient in terms of costs.

In addition, the fullerene derivative according to an exemplary embodiment of the present disclosure may be in the form of a film having a thin film form such as a single crystal.

When an organic thin film layer is formed, the fullerene derivative according to an exemplary embodiment of the present disclosure has an excellent effect of enhancing the morphology due to an increase in solubility, so that charges may be effectively moved.

The fullerene derivative according to an exemplary embodiment of the present disclosure may be fabricated by a fabrication method to be described below.

The fullerene derivative of Formula 1 may be obtained by reacting arylhydrazide with a carbonyl group (ketone C=O) in an alkylalcohol such as ethanol or methanol as in the following reaction condition A to form an imine group which is a double bond of C=N, and then forming a carbon-carbon bond in a carbon cluster compound of Cn as in the reaction condition B.

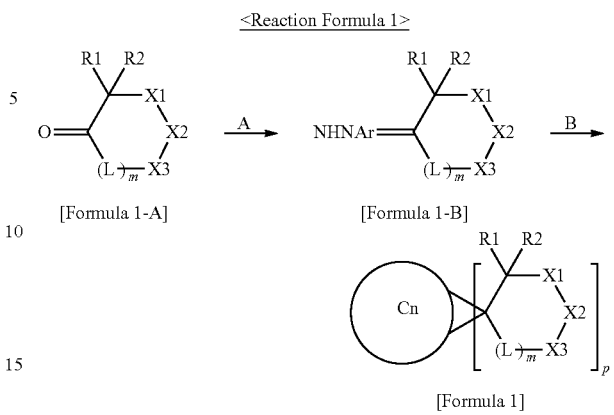

Reaction Condition A
1) Aromatic hydrazine ($ArNHNH_2$), a small amount of $H_2SO_4$ or HCl, alkylalcohol, reflux
2) Filtration, or extraction
3) Purification A cyclic ketone-based compound and a substituted or unsubstituted aromatichydrazine were stirred while being heated for 3 hours to 24 hours in methanol or ethanol, and a solid formed was filtered, and then dried or purified.

Reaction Condition B
1) $C_{60}$, 1,2-dichlorobenzene or chlorobenzene, and pyridine
2) Addition of sodium methoxide ($NaOCH_3$)
3) Stirring at 180° C.
4) An excessive amount of the solvent was removed, and then the residue was purified by column chromatography.

In an exemplary embodiment of the present disclosure, provided is an organic solar cell including: a first electrode; a second electrode provided to face the first electrode; and an organic material layer including one or more layers, which is provided between the first electrode and the second electrode and includes a photoactive layer, in which one or more layers of the organic material layer includes the fullerene derivative.

FIG. 1 is a view illustrating the organic solar cell according to an exemplary embodiment of the present disclosure. FIG. 1 includes a substrate 101, a first electrode 102, a hole transport layer 103, a photoactive layer 104, and a second electrode 105.

According to the principle of the organic solar cell, a p-type semiconductor forms an exciton in which an electron and a hole form a pair by photoexcitation, and the exciton is divided into an electron and a hole in the p-n junction portion. The separated electron and hole move to an n-type semiconductor thin film and a p-type semiconductor thin film, respectively, and these are collected in the first electrode and the second electrode, respectively, and thus may be externally used as an electric energy.

In an exemplary embodiment of the present disclosure, the organic material layer includes a hole transport layer, a hole injection layer, or a layer which transports and injects holes simultaneously, and the hole transport layer, the hole injection layer, or the layer which transports and injects holes simultaneously includes the fullerene derivative.

In an exemplary embodiment of the present disclosure, the organic material layer includes an electron injection layer, an electron transport layer, or a layer which injects and transports electrons simultaneously, and the electron injection layer, the electron transport layer, or the layer which injects and transports electrons simultaneously includes the fullerene derivative.

In an exemplary embodiment of the present disclosure, the organic material layer includes a photoactive layer, and the photoactive layer includes the fullerene derivative.

In an exemplary embodiment of the present disclosure, the photoactive layer includes one or two or more selected from the group consisting of an electron donor and an electron acceptor, and the electron acceptor includes the fullerene derivative.

In an exemplary embodiment of the present disclosure, the electron donor and the electron acceptor constitute a bulk heterojunction (BHJ).

The bulk heterojunction means that an electron donor material and an electron acceptor material are mixed with each other in a photoactive layer.

In an exemplary embodiment of the present disclosure, the organic material layer includes a photoactive layer, the photoactive layer has a bilayer thin film structure including an n-type organic material layer and a p-type organic material layer, and the n-type organic material layer includes the fullerene derivative.

In an exemplary embodiment of the present disclosure, the organic solar cell may further include one or two or more organic material layers from the group consisting of a hole injection layer, a hole transport layer, a hole blocking layer, a charge generation layer, an electron blocking layer, an electron injection layer, and an electron transport layer.

In the fullerene derivative according to an exemplary embodiment of the present disclosure, an electron acceptor material which is excellent in solubility with respect to an organic solvent may be efficiently prepared by a simple preparation method. Furthermore, since it is possible to use a material which may have photoreactivity, photostability and conductivity as a starting material, an electron acceptor material having high solubility during the reaction may be prepared.

In an exemplary embodiment of the present disclosure, the n-type organic material layer and/or the electron donor material are/is preferably those which are suitable for a light absorption wavelength range or a solar spectrum, have strong light absorbance, and have excellent electrical properties such as mobility of charges, and it is possible to use a single molecule or a polymer, which enables a solution process.

According to an exemplary embodiment of the present disclosure, the electron donor material may include: at least one electron donor; or a polymer of at least one electron acceptor and at least one electron donor. The electron donor material may include at least one electron donor. In addition, the electron donor material includes a polymer of at least one electron acceptor and at least one electron donor.

Specifically, the electron donor material may be various polymer materials such as thiophene-based, fluorene-based, and carbazole-based materials, and a single molecular material, starting from MEH-PPV (poly[2-methoxy-5-(2'-ethylhexyloxy)-1,4-phenylene vinylene].

Specifically, the single molecular material may include one or more materials selected from the group consisting of copper (II) phthalocyanine, zinc phthalocyanine, tris[4-(5-dicyanomethylidenemethyl-2-thienyl)phenyl]amine, 2,4-bis[4-(N,N-dibenzylamino)-2,6-dihydroxyphenyl]squaraine, benz[b]anthracene, and pentacene.

Specifically, the polymer material may include one or more materials selected from the group consisting of poly 3-hexyl thiophene (P3HT), poly[N-9'-heptadecanyl-2,7-carbazole-alt-5,5-(4'-7'-di-2-thienyl-2',1',3'-benzothiadiazole)] (PCDTBT), poly[2,6-(4,4-bis-(2,ethylhexyl)-4H-cyclopenta[2,1-b;3,4-b']dithiophene)-alt-4,7-(2,1,3-benxothiadiazole)] (PCPDTBT), poly[2,7-(9,9-dioctyl-fluorene)-alt-5,5-(4,7-di 2-thienyl-2,1,3-benzothiadiazole)] (PFO-DBT), poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7), and poly[2,7-(9,9-dioctyl-dibenzosilole)-alt-4,7-bis(thiophen-2-yl)benzo-2,1,3-thiadiazole] (PSiF-DBT).

The electron donor materials are preferably materials having a small band gap such that the entire region of the visible light of the solar light may be absorbed, and are generally a polymer compound, but are not limited thereto.

The electron donor material and the electron acceptor material are mixed at a ratio (w/w) of 1:10 to 10:1. In order to maximize characteristics after the electron donor material and the electron acceptor material are mixed, an annealing process may be performed at 30 to 300° C. for 1 second to 24 hours.

In an exemplary embodiment of the present disclosure, the photoactive layer has a thickness of 10 nm to 1,000 nm. After the photoactive materials as described above are dissolved in an organic solvent, the solution is introduced into a photoactive layer by a method such as spin coating. In this case, it is possible to apply a method such as dip coating, screen printing, spray coating, doctor blade, and brush painting to the photoactive layer.

In an exemplary embodiment of the present disclosure, the first electrode may be an anode electrode, and a cathode electrode. Furthermore, the second electrode may be a cathode electrode, and an anode electrode.

In an exemplary embodiment of the present disclosure, in organic solar cell, an anode electrode, a photoactive layer, and a cathode electrode may be arranged in this order.

In another exemplary embodiment, the cathode electrode, the photoactive layer, and the anode electrode may also be arranged in this order, but the order is not limited thereto.

In still another exemplary embodiment, in the organic solar cell, the anode electrode, the hole transport layer, the photoactive layer, the electron transport layer, and the cathode electrode may also be arranged in this order, and the cathode electrode, the electron transport layer, the photoactive layer, the hole transport layer, and the anode electrode may also be arranged in this order, but the order is not limited thereto.

In yet another exemplary embodiment, in the organic solar cell, an anode electrode, a buffer layer, a photoactive layer, and a cathode electrode may be arranged in this order.

The organic solar cell of the present disclosure may be fabricated by materials and methods known in the art, except that the fullerene derivative represented by Formula 1 is included in one or more layers in the organic material layer of the organic solar cell.

In an exemplary embodiment of the present disclosure, provided is a method for fabricating an organic solar cell, the method including: preparing a substrate; forming a first electrode on an upper portion of the substrate; forming an organic material layer including one or more layers, which includes a photoactive layer on an upper portion of the first electrode; and forming a second electrode on an upper portion of the organic material layer, in which the organic material layer including one or more layers includes the fullerene derivative.

Specifically, in an exemplary embodiment of the present disclosure, the method may include preparing a substrate, forming an anode on an upper portion of the substrate, forming a hole transport layer on the anode, forming a photoactive layer on the hole transport layer, forming an electron transport layer on the photoactive layer, and forming a cathode on the electron transport layer.

In another exemplary embodiment, the method may include preparing a substrate, forming a cathode on an upper portion of the substrate, forming an electron transport layer on the cathode, forming a photoactive layer on the electron transport layer, forming a hole transport layer on the photoactive layer, and forming an anode on the hole transport layer.

The organic solar cell of the present disclosure may be fabricated, for example, by sequentially stacking an anode, a photoactive layer, and a cathode on a substrate.

The fullerene derivative may be included in the hole transport layer; the photoactive layer; and/or the electron transport layer.

For example, the organic solar cell according to the present invention may be fabricated by depositing a metal or a metal oxide having conductivity, or an alloy thereof on a substrate to form an anode by using a physical vapor deposition (PVD) method such as sputtering or e-beam evaporation, forming an organic material layer thereon by vacuum deposition or a solution application method, and then depositing a material which may be used as a cathode thereon.

Each of the organic material layers may be fabricated by a solvent process using various single molecular to polymer materials instead of a deposition method, for example, a method such as roll to roll, spin coating, dip coating, casting, roll coat, flow coating, doctor blading, screen printing, inkjet printing, gravure printing, offset printing, spray coating, or a thermal transfer method.

The organic material layer of each layer may be fabricated by a method, such as a dry film forming method, such as vacuum deposition, sputtering, plasma, and ion plating.

In an exemplary embodiment of the present disclosure, the method may include depositing an anode, stacking a photoactive layer, arranging a photoactive layer, subjecting the photoactive layer to heat treatment, and depositing a cathode.

In the stacking of the photoactive layer, a composite thin film structure deposited by spraying a solution in which an electron donor material and an electron acceptor material are mixed, that is, a bulk heterojunction may be disposed at the upper side of a positive electrode.

In the electron acceptor material, a mixture solution in which a composite polymer material is dissolved in an organic solvent may be used, and the fullerene derivative may be included.

In an exemplary embodiment of the present disclosure, P3HT is dissolved in an organic solvent, and used in the fullerene derivative.

In the present disclosure, the substrate may be a glass substrate or a transparent plastic substrate having excellent transparency, surface smoothness, handleability, and water proof properties, but is not limited thereto, and is not limited as long as the substrate is a substrate typically used in an organic solar cell. Specific examples thereof include glass or polyethylene terephthalate (PET), polyethylene naphthalate (PEN), polypropylene (PP), polyimide (PI), triacetyl cellulose (TAC), and the like, but are not limited thereto.

The anode electrode may be a material which is transparent and has excellent conductivity, but is not limited thereto. Examples thereof include: a metal, such as vanadium, chromium, copper, zinc, or gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

A method of forming the anode electrode is not particularly limited, but the anode electrode may be formed, for example, by applying a solution on one surface of a substrate using sputtering, e-beam, thermal deposition, spin coating, screen printing, inkjet printing, doctor blade, or a gravure printing method, or coating the solution in the form of a film.

When the anode electrode is formed on a substrate, the anode electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a heating plate at 100 to 150° C. for 1 to 30 minutes, preferably at 120° C. for 10 minutes in order to remove moisture, and when the substrate is completely cleaned, the surface of the substrate is hydrophilically modified.

Through the surface modification as described above, the junction surface potential may be maintained at a level suitable for a surface potential of a photoactive layer. Further, during the modification, a polymer thin film is easily formed on an anode electrode, and the quality of the thin film may also be enhanced.

Examples of a pre-treatment technology for an anode electrode include a) a surface oxidation method using a parallel flat plate-type discharge, b) a method of oxidizing the surface through ozone produced by using UV (ultraviolet) rays in a vacuum state, c) an oxidation method using oxygen radicals produced by plasma, and the like.

One of the methods may be selected according to the state of the anode electrode or the substrate. However, even though any method is used, it is preferred that oxygen is commonly prevented from being separated from the surface of the anode electrode or the surface, and moisture and organic materials are maximally inhibited from remaining. In this case, it is possible to maximize a substantial effect of the pre-treatment.

As a specific example, it is possible to use a method of oxidizing the surface through ozone produced by using UV. In this case, an ITO substrate patterned after being ultrasonically cleaned is baked on a hot plate and dried well, and then introduced into a chamber, and the ITO substrate patterned may be cleaned by ozone generated by reacting an oxygen gas with UV light by operating an UV lamp.

However, the surface modification method of the ITO substrate patterned in the present disclosure needs not be particularly limited, and any method may be used as long as the method is a method of oxidizing a substrate.

The cathode electrode may be a metal having a low work function, but is not limited thereto. Specific examples thereof include: a metal, such as magnesium, calcium, sodium, potassium, titanium, indium, yttrium, lithium, gadolinium, aluminum, silver, tin, and lead, or alloys thereof; and a multi-layered material, such as LiF/Al, $LiO_2$/Al, LiF/Fe, Al:Li, Al:$BaF_2$, and Al:$BaF_2$:Ba, but are not limited thereto.

The cathode electrode may be deposited and formed in a thermal evaporator showing a vacuum degree of $5\times10^{-7}$ torr or less, but is not limited to this method.

The hole transport layer and/or electron transport layer materials serve to efficiently transfer electrons and holes separated from a photoactive layer to the electrode, and the material is not particularly limited.

The hole transport layer material may be poly(3,4-ethylenediocythiophene) doped with poly(styrenesulfonic acid) (PEDOT:PSS) and molybdenum oxide ($MoO_x$); vanadium oxide ($V_2O_5$); nickel oxide (NiO); and tungsten oxide ($WO_x$), and the like, but is not limited thereto.

The electron transport layer material may be electron-extracting metal oxides, and specific examples thereof include: a metal complex of 8-hydroxyquinoline; a complex including $Alq_3$; a metal complex including Liq; LiF; Ca; titanium oxide ($TiO_x$); zinc oxide (ZnO); and cesium carbonate ($Cs_2CO_3$), and the like, but are not limited thereto.

The photoactive layer may be formed by dissolving a photoactive material such as an electron donor and/or an electron acceptor in an organic solvent, and then applying the solution by a method such as spin coating, dip coating, screen printing, spray coating, doctor blade, and brush painting, but the method is not limited thereto.

BEST MODE

A fabrication method of the fullerene derivative and the fabrication of an organic solar cell using the same will be described in detail in the following Preparation Examples and Examples. However, the following Examples are provided for illustrating the present disclosure, and the range of the present disclosure is not limited thereby.

Preparation Example 1-1-1

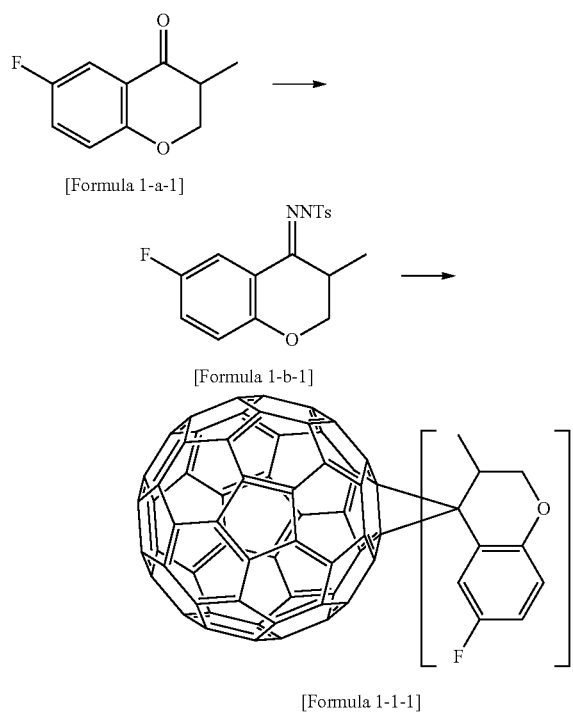

[Formula 1-1-1]

6-fluoro-2-methyl-4-chromanone (3.6 g, 19.98 mmol), p-toluensulfonylhydrazide (4.09 g, 21.98 mmol), 200 ml of ethanol, and sulfuric acid ($H_2SO_4$) (1 ml) were put thereinto, and the resulting mixture was stirred for 24 hours. The mixture solution was stirred while being heated for 18 hours. After the reaction temperature was lowered to room temperature, a white solid formed was filtered and dried, thereby obtaining a compound of Formula 1-b-1 (6.74 g, yield 96.9%).

C60 (7.2 g, 2 eq. 10 mmol), o-dichloro benzene (100 ml), pyridine (20 ml), sodium methoxide ($NaOCH_3$) (2 eq. 10 mmol, 0.54 g) were put thereinto, and the resulting mixture was stirred while being heated at 120° C. Formula 1-b-1 (0.96 g, 3.85 mmol) was put into the mixture and warmed to 170° C., and then the resulting mixture was stirred for 2 hours. After the temperature of the reaction solution was lowered to room temperature, the solid which had not been dissolved was filtered through a filter paper, and then the organic solvent was removed by vacuum distillation. The resulting mixture was diluted with a small amount of o-dichlorobenzene (ODCB), and then loaded to a silica gel column, and developed with n-hexane to remove o-dichlorobenzene (ODCB) and partially dissolved C60. Subsequently, the residue was developed with toluene and purified. After the solvent was removed by vacuum distillation, a solid was obtained by forming a precipitate using methanol, and then a compound (380 mg, yield 4.5%) of Formula 1-1-1 was prepared by drying the solid.

248 mg of a compound with p=2 was obtained by purifying the prepared compound by column chromatography.

The mass analysis result of the compound is as follows.

MS: m/z n=1: 884, n=2: 1,048

Preparation Example 1-1-2

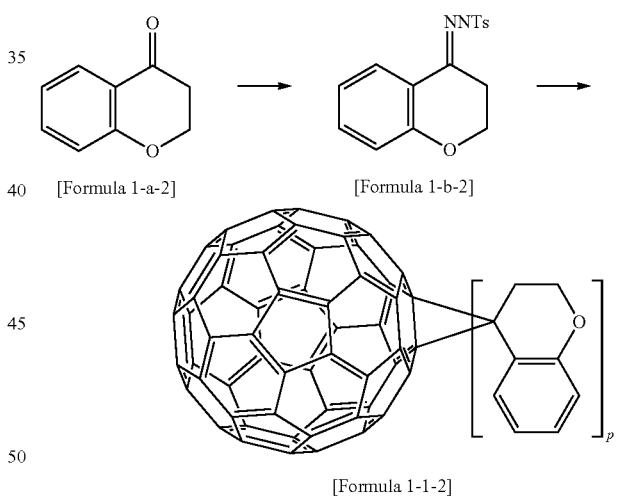

[Formula 1-1-2]

A compound of Formula 1-b-2 was prepared by performing reaction by the same method, except that a compound 4-chromanone and methanol were used instead of 6-fluoro-2-methyl-4-chromanone which is the compound of Preparation Example 1-1-1 and ethanol, respectively.

A compound of Formula 1-1-2 was prepared by performing reaction by the same method as in the preparation method of Formula 1-1-1 of Preparation Example 1-1-1, except that Formula 1-b-2 was used instead of Formula 1-a-2.

The mass analysis result of the compound is as follows.

MS: m/z p=1: 867, p=2: 983

Preparation Example 1-1-3

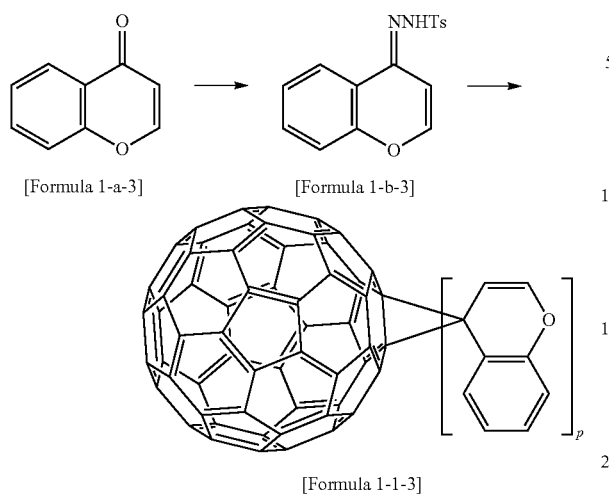

A compound of Formula 1-b-3 was prepared by performing reaction by the same method, except that a compound 4H-chromen-4-one and ethanol were used instead of 6-fluoro-2-methyl-4-chromanone which is the compound of Preparation Example 1-1-1.

A compound of Formula 1-1-3 was prepared by performing reaction by the same method as in the preparation method of Formula 1-1-1 of Preparation Example 1-1-1, except that Formula 1-b-3 was used instead of Formula 1-b-1.

The mass analysis result of the compound is as follows.
MS: m/z p=1: 865 p=2: 979

Preparation Example 1-1-4

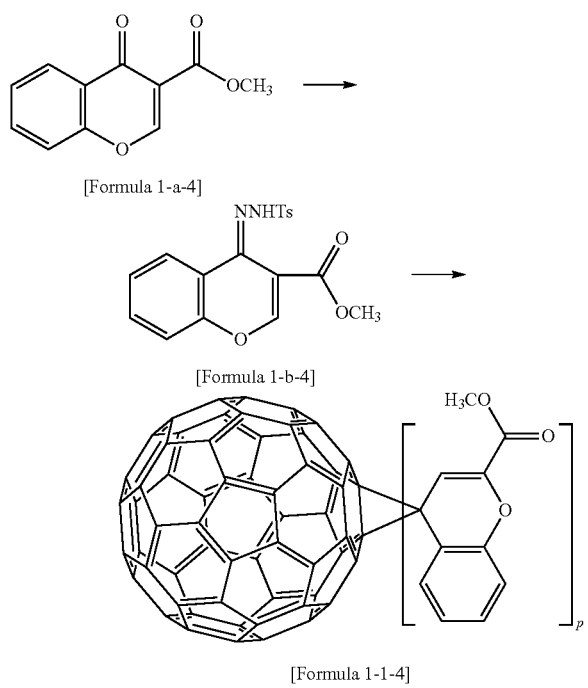

A compound of Formula 1-b-4 was prepared by performing reaction by the same method, except that a compound methyl 4-oxo-4H-chromene-3-carboxylate and ethanol were used instead of 6-fluoro-2-methyl-4-chromanone which is the compound of Preparation Example 1-1-1.

A compound of Formula 1-1-4 was prepared by performing reaction by the same method as in the preparation method of Formula 1-1-1 of Preparation Example 1-1-1, except that Formula 1-b-3 was used instead of Formula 1-b-1.

The mass analysis result of the compound is as follows.
MS: m/z p=1: 865 p=2: 979

Preparation Example 1-1-5

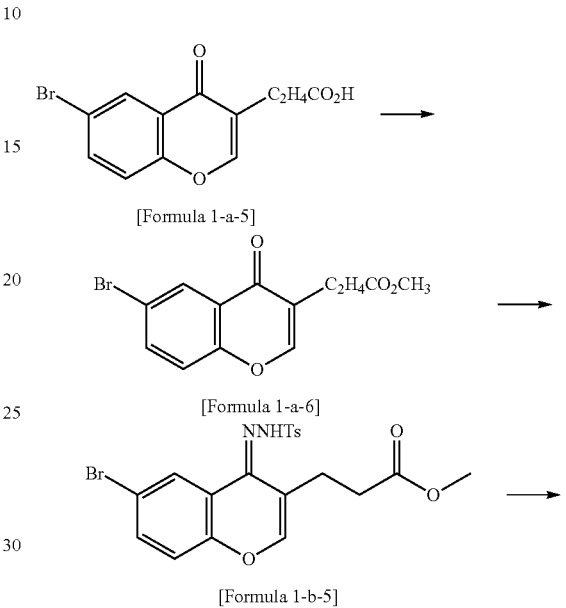

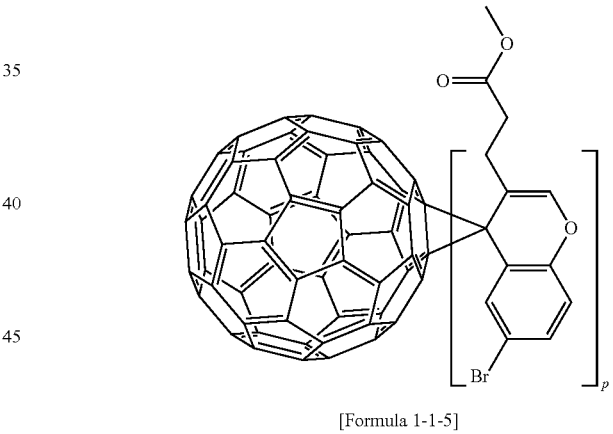

A compound of Formula 1-a-5 which is 6-bromochromone-3-propionic acid and an excessive amount of methanol (MeOH) were put thereinto, and a small amount of sulfuric acid was put into the container, and the mixture was stirred while being heated. The reactant was cooled to room temperature, and the compound of 1-a-6 was synthesized by column chromatography.

A compound of Formula 1-b-5 was prepared by performing reaction by the same method, except that Compound 1-a-6 was used instead of 6-fluoro-2-methyl-4-chromanone which is the compound of Preparation Example 1-1-1.

A compound of Formula 1-1-5 with p=1 was prepared by performing reaction by the same method as in the preparation method of Formula 1-1-1 of Preparation Example 1-1-1, except that Formula 1-b-5 was used instead of Formula 1-b-1.

The mass analysis result of the compound is as follows.
MS: m/z p=1: 1044

Preparation Example 1-1-6

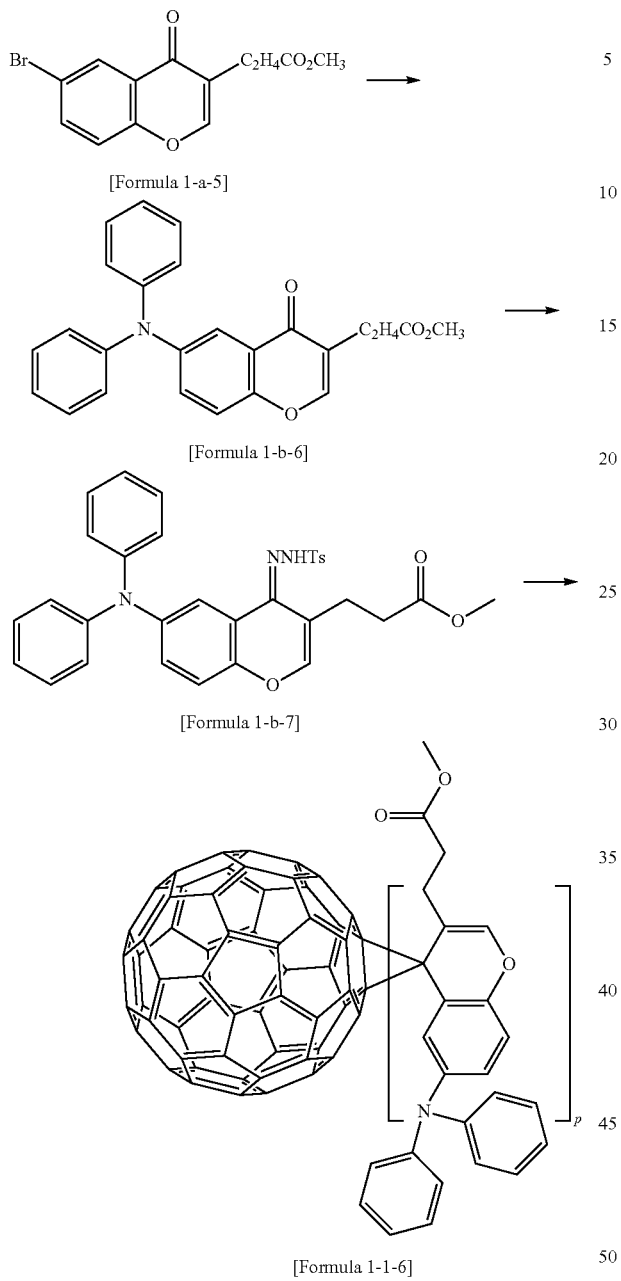

Compound 1-a-5 (6.26 g, 20.2 mmol) and diphenylamine (3.8 g, 22.5 mmol) were dissolved in 200 mL of xylene, sodium-tertiary-butoxide (2.9 g, 30.2 mmol) and Pd[P(t-Bu)$_3$]$_2$ (0.20 g, 0.40 mmol) were added thereto, and then the resulting mixture was stirred while being heated under nitrogen flow for 5 hours. Distilled water was put into the reaction solution, the reaction was terminated, and the organic layer was extracted. After column separation was performed by using a solvent of normal-hexane/ethyl acetate=10/1 (volume ratio), Compound 1-b-6 (6.13 g, yield 76%) was prepared by performing stirring in a petroleum ether, and then drying the residue under vacuum.

MS: [M+H]+=400

A compound of Formula 1-b-7 was prepared by performing reaction by the same method, except that Compound 1-b-6 was used instead of 6-fluoro-2-methyl-4-chromanone which is the compound of Preparation Example 1-1-1.

A compound of Formula 1-1-6 with p=1 was prepared by performing reaction by the same method as in the preparation method of Formula 1-1-1 of Preparation Example 1-1-1, except that Formula 1-b-7 was used instead of Formula 1-b-1.

The mass analysis result of the compound is as follows.
MS: m/z p=1: 1701

Preparation Example 1-1-7

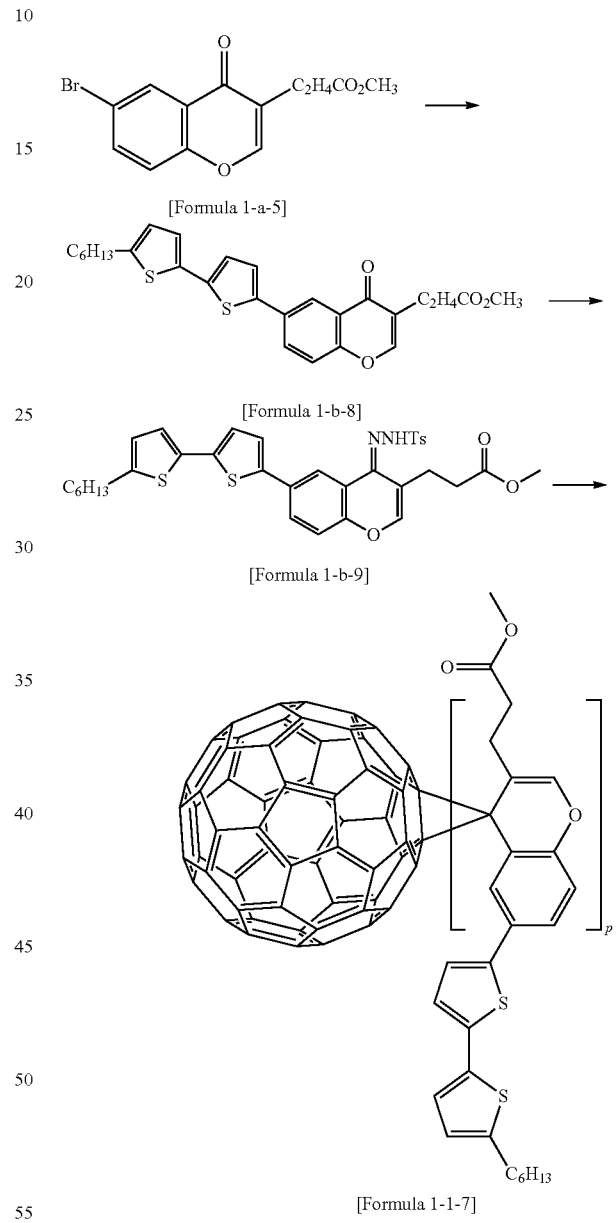

Compound 1-a-5 (6.26 g, 20.2 mmol), 5'-hexyl-[2,2'-bithiophen]-5-yl)trimethylstannane (10.8 g, 22.5 mmol), and Pd(PPh$_3$)$_4$ (0.05 g, 0.04 mmol) were stirred while being heated under nitrogen flow in 200 mL of toluene for 12 hours. After the reactant was cooled to room temperature, distilled water was put into the reaction solution, the reaction was terminated, and the organic layer was extracted. After column separation was performed by using a solvent of normal-hexane/ethyl acetate=6/1 (volume ratio), Compound 1-b-8 (4.17 g, yield 43%) was prepared by performing recrystallization using normal-hexane.

MS: [M+H]+=481

A compound of Formula 1-b-9 was prepared by performing reaction by the same method, except that Compound 1-b-8 was used instead of 6-fluoro-2-methyl-4-chromanone which is the compound of Preparation Example 1-1-1.

A compound of Formula 1-1-7 with p=1 was prepared by performing reaction by the same method as in the preparation method of Formula 1-1-1 of Preparation Example 1-1-1, except that Formula 1-b-9 was used instead of Formula 1-b-1.

The mass analysis result of the compound is as follows.
MS: m/z p=1: 1864

Preparation Example 1-1-8

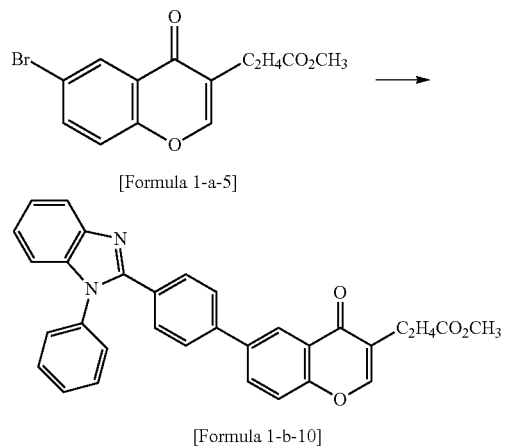

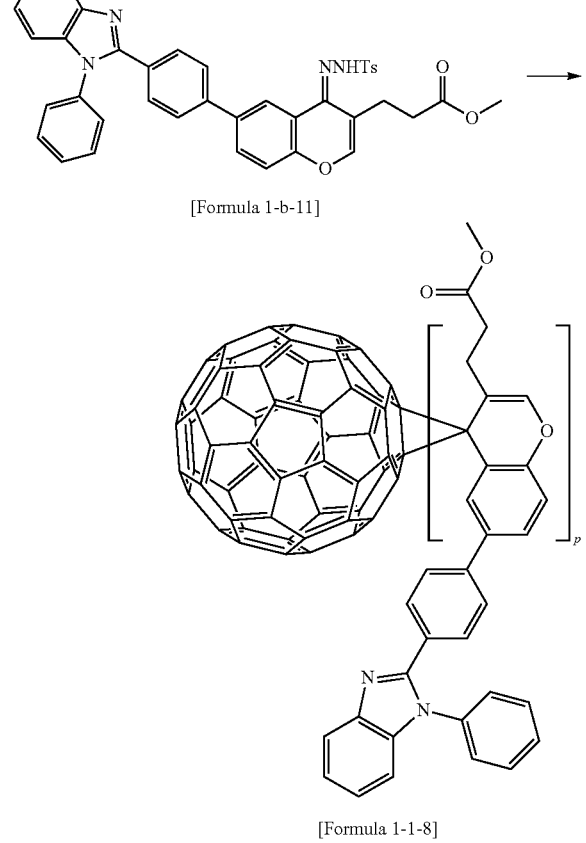

Compound 1-2-5 (6.26 g, 20.2 mmol), 1-phenyl-2-(4-(4,4,5,5-tetramethyl-1,3,2-dioxaborolan-2-yl)phenyl)-1H-benzo[d]imidazole (9.0 g, 22.5 mmol), and Pd(PPh$_3$)$_4$ (0.05 g, 0.04 mmol) were stirred while being heated under nitrogen flow in 150 mL of toluene and 50 mL of an aqueous NaHCO$_3$ solution for 12 hours. After the reactant was cooled to room temperature, distilled water was put into the reaction solution, and the organic layer was extracted. After column separation was performed by using a solvent of normal-hexane/ethyl acetate=4/1 (volume ratio), Compound 1-b-10 (3.55 g, yield 71%) was prepared by performing recrystallization using ethanol.

MS: [M+H]+=501

A compound of Formula 1-b-11 was prepared by performing reaction by the same method, except that Compound 1-b-10 was used instead of 6-fluoro-2-methyl-4-chromanone which is the compound of Preparation Example 1-1-1.

A compound of Formula 1-1-8 with p=1 was prepared by performing reaction by the same method as in the preparation method of Formula 1-1-1 of Preparation Example 1-1-1, except that Formula 1-b-11 was used instead of Formula 1-b-1.

The mass analysis result of the compound is as follows.
MS: m/z p=1: 1235

Preparation Example 1-1-9

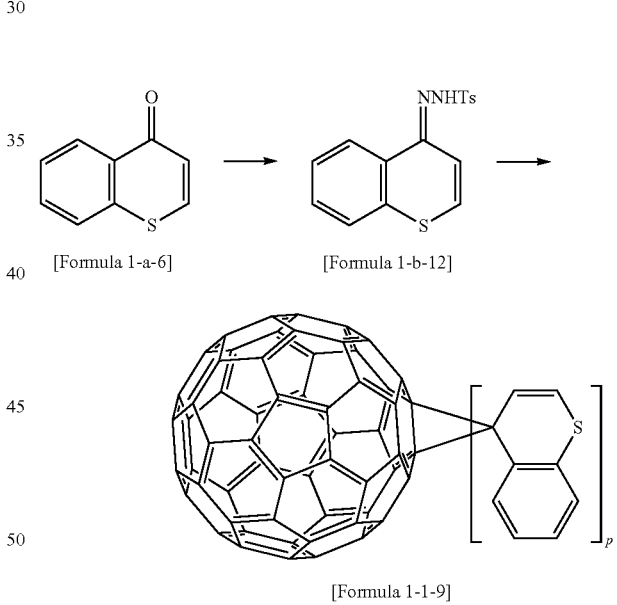

Compound 1-b-12 was prepared by performing reaction by the same method, except that a compound thiochromen-4-one was used instead of 6-fluoro-2-methyl-4-chromanone which is the compound of Preparation Example 1-1-1.

A compound of Formula 1-1-9 was prepared by performing reaction by the same method as in the preparation method of Formula 1-1-1 of Preparation Example 1-1-1, except that Formula 1-b-12 was used instead of Formula 1-b-1.

The mass analysis result of the compound is as follows.
MS: m/z p=2: 1043

Preparation Example 1-1-10

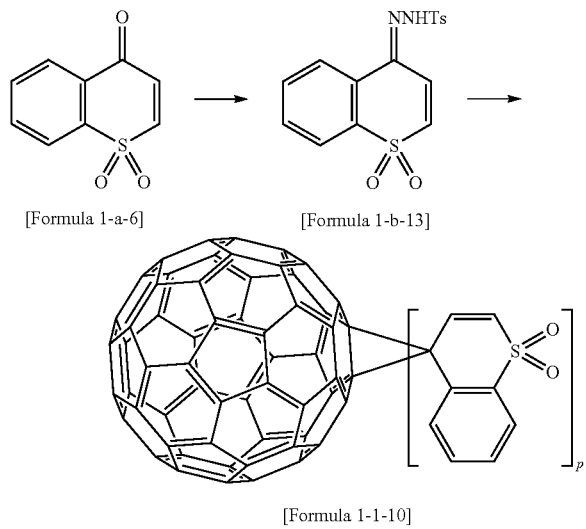

[Formula 1-1-10]

Compound 1-b-13 was prepare by performing reaction by the same method, except that a compound 4H-1-benzothiopyran-4-one 1,1-dioxide was used instead of 6-fluoro-2-methyl-4-chromanone which is the compound of Preparation Example 1-1-1.

In the preparation method of Formula 1-1-1 of Preparation Example 1-1-1, a compound of Formula 1-1-10 was prepared by performing reaction by the same method, except that Formula 1-b-13 was used instead of Formula 1-b-1.

The mass analysis result of the compound is as follows.
MS: m/z p=1: 928

In order to observe electrochemical characteristics of the compounds prepared in the Preparation Examples, oxidation/reduction characteristics were observed by using a cyclic voltammetry (CV).

AUTOLAB was used as the CV apparatus, a 0.1 M solution prepared by dissolving tetrabutylammonium tetrafluoroborate ($Bu_4NBF_4$) in acetonitrile was used as an electrolyte, and a solvent capable of dissolving a sample at a concentration of $10^{-3}$ M was selected and dissolved the sample.

A glass carbon electrode was used as a working electrode, Pt and Ag/AgCl electrodes were used as a counter electrode and a reference electrode, respectively, and as a result, the LUMO energy levels of the compounds of Preparation Examples 1-1-1 to 1-1-10 satisfying the structure of Formula 1 were observed within 3.5 eV to 4.0 eV. Accordingly, the compounds have a preferred LUMO energy level, and have characteristics which might be utilized in an organic solar cell.

On the contrary, when a substituent which sufficiently attracts electrons is introduced, the LUMO energy level value will have a value deeper than 4.0 eV. On the contrary, when a substituent which sufficiently pushes electrons is introduced, the compounds may also be prepared so as to have LUMO energy levels higher than 3.5 eV.

Fabrication of Organic Solar Cell and Measurement of Characteristics Thereof

The organic solar cells were fabricated as described below by using the compounds prepared in Preparation Examples 1-1-1 to 1-1-10 and Comparative Example 1, photoelectric conversion characteristics of the organic solar cells were measured under the 100 mW/cm² (AM 1.5) conditions, and the results are shown in the following Table 1.

<Example 1> Fabrication of Organic Solar Cell

A composite solution was prepared by dissolving the compound prepared in Preparation Example 1-1-1 and P3HT at a ratio of 0.7:1 in chlorobenzene (CB). In this case, the concentration was adjusted to 2.0 wt %, and the organic solar cell was allowed to have a structure of ITO/PEDOT:PSS/a photoactive layer/Al. A glass substrate coated with ITO was ultrasonically washed using distilled water, acetone, and 2-propanol, and the ITO surface was treated with ozone for 10 minutes, and then heat treatment was performed, followed by heat treatment at 120° C. for 10 minutes by spin-coating PEDOT:PSS (baytrom P) with a thickness of 45 nm. For coating of the photoactive layer, a compound-PCBM composite solution was filtered with a 0.45 μm PP syringe filter and spin-coated, and then an organic solar cell was fabricated by depositing Al with a thickness of 200 nm using a thermal evaporator under a vacuum of $3 \times 10^{-8}$ torr.

<Example 2> Fabrication of Organic Solar Cell

A composite solution was prepared by dissolving the compound prepared in Preparation Example 1-1-2 and P3HT at a ratio of 1:1 in chlorobenzene (CB). In this case, the concentration was adjusted to 2.0 wt %, and the organic solar cell was allowed to have a structure of ITO/PEDOT:PSS/a photoactive layer/Al. A glass substrate coated with ITO was ultrasonically washed using distilled water, acetone, and 2-propanol, the ITO surface was treated with ozone for 10 minutes, followed by heat treatment at 120° C. for 10 minutes by spin-coating PEDOT:PSS (baytrom P) with a thickness of 45 nm. For coating of the photoactive layer, a compound-PCBM composite solution was filtered with a 0.45 μm PP syringe filter and spin-coated, and then an organic solar cell was fabricated by depositing Al with a thickness of 200 nm using a thermal evaporator under a vacuum of $3 \times 10^{-8}$ torr.

<Example 3> Fabrication of Organic Solar Cell

A composite solution was prepared by dissolving the compound prepared in Preparation Example 1-1-1 and the following Formula 2-1-1 at a ratio of 1:1 in chlorobenzene (CB). In this case, the concentration was adjusted to 2.0 wt %, and the organic solar cell was allowed to have a structure of ITO/PEDOT:PSS/a photoactive layer/Al. A glass substrate coated with ITO was ultrasonically washed using distilled water, acetone, and 2-propanol, the ITO surface was treated with ozone for 10 minutes, followed by heat treatment at 120° C. for 10 minutes by spin-coating PEDOT:PSS (baytrom P) with a thickness of 45 nm. For coating of the photoactive layer, a compound-PCBM composite solution was filtered with a 0.45 μm PP syringe filter and spin-coated, and then an organic solar cell was fabricated by depositing Al with a thickness of 200 nm using a thermal evaporator under a vacuum of $3 \times 10^{-8}$ torr.

[Formula 2-1-1]

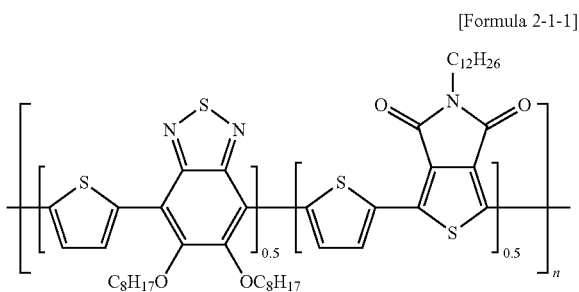

<Example 4> Fabrication of Organic Solar Cell

A composite solution was prepared by dissolving the compound prepared in Preparation Example 1-1-2 and the following Formula 2-1-1 at a ratio of 1:1 in chlorobenzene (CB). In this case, the concentration was adjusted to 2.0 wt %, and the organic solar cell was allowed to have a structure of ITO/PEDOT:PSS/a photoactive layer/Al. A glass substrate coated with ITO was ultrasonically washed using distilled water, acetone, and 2-propanol, the ITO surface was treated with ozone for 10 minutes, followed by heat treatment at 120° C. for 10 minutes by spin-coating PEDOT:PSS (baytrom P) with a thickness of 45 nm. For coating of the photoactive layer, a compound-PCBM composite solution was filtered with a 0.45 μm PP syringe filter and spin-coated, and then an organic solar cell was fabricated by depositing Al with a thickness of 200 nm using a thermal evaporator under a vacuum of $3\times10^{-8}$ torr.

[Formula 2-1-1]

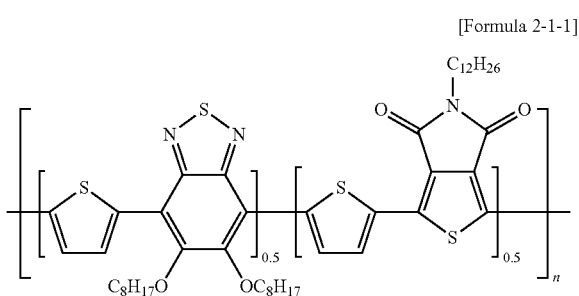

Example 5

An organic solar cell was fabricated by the same method as in Example 3, except that Formula 1-1-3 was used instead of Formula 1-1-1.

Example 6

An organic solar cell was fabricated by the same method as in Example 3, except that Formula 1-1-4 was used instead of Formula 1-1-1.

Example 7

An organic solar cell was fabricated by the same method as in Example 3, except that Formula 1-1-5 was used instead of Formula 1-1-1.

Example 8

An organic solar cell was fabricated by the same method as in Example 3, except that Formula 1-1-6 was used instead of Formula 1-1-1.

Example 9

An organic solar cell was fabricated by the same method as in Example 3, except that Formula 1-1-7 was used instead of Formula 1-1-1.

Example 10

An organic solar cell was fabricated by the same method as in Example 3, except that Formula 1-1-8 was used instead of Formula 1-1-1.

Example 11

An organic solar cell was fabricated by the same method as in Example 2, except that Formula 1-1-9 was used instead of Formula 1-1-2.

Example 12

An organic solar cell was fabricated by the same method as in Example 2, except that Formula 1-1-10 was used instead of Formula 1-1-2.

<Comparative Example 1> Fabrication of Organic Solar Cell

A composite solution was prepared by dissolving P3HT and PCBM at a ratio of 1:1 in 1,2-dichlorobenzene (DCB). In this case, the concentration was adjusted to 1.0 to 2.0 wt %, and the organic solar cell was allowed to have a structure of ITO/PEDOT:PSS/a photoactive layer/LiF/Al. A glass substrate coated with ITO was ultrasonically washed using distilled water, acetone, and 2-propanol, the ITO surface was treated with ozone for 10 minutes, followed by heat treatment at 120° C. for 10 minutes by spin-coating PEDOT:PSS (baytrom P) with a thickness of 45 nm. For coating of the photoactive layer, a compound-PCBM composite solution was filtered with a 0.45 μm PP syringe filter and spin-coated, heat treatment was performed at 120° C. for 5 minutes an organic solar cell was fabricated by depositing LiF with a thickness of 7 Å, and then Al with a thickness of 200 nm using a thermal evaporator under a vacuum of $3\times10^{-8}$ torr.

TABLE 1

| | Active layer (Electron donor:Electron acceptor) | $V_{OC}$ (V) | $J_{SC}$ (mA/cm$^2$) | FF | η (%) |
|---|---|---|---|---|---|
| Example 1 | P3HT:Formula 1-1-1 = 1:0.7 | 0.62 | 9.854 | 0.55 | 3.41 |
| Example 2 | P3HT:Formula 1-1-2 = 1:1 | 0.62 | 9.646 | 0.56 | 3.37 |
| Example 3 | Formula 2-1-1:Formula 1-1-1 = 1:1 | 0.82 | 11.646 | 0.56 | 5.37 |
| Example 4 | Formula 2-1-1:Formula 1-1-2 = 1:1 | 0.80 | 10.156 | 0.60 | 4.91 |
| Example 5 | Formula 2-1-1:Formula 1-1-3 = 1:1 | 0.85 | 10.211 | 0.54 | 4.72 |

TABLE 1-continued

| | Active layer (Electron donor:Electron acceptor) | $V_{OC}$ (V) | $J_{SC}$ (mA/cm$^2$) | FF | η (%) |
|---|---|---|---|---|---|
| Example 6 | Formula 2-1-1:Formula 1-1-4 = 1:1 | 0.80 | 10.006 | 0.60 | 4.88 |
| Example 7 | Formula 2-1-1:Formula 1-1-5 = 1:1 | 0.84 | 9.981 | 0.62 | 5.23 |
| Example 8 | Formula 2-1-1:Formula 1-1-6 = 1:1 | 0.84 | 9.897 | 0.58 | 4.89 |
| Example 9 | Formula 2-1-1:Formula 1-1-7 = 1:1 | 0.87 | 10.005 | 0.62 | 5.48 |
| Example 10 | Formula 2-1-1:Formula 1-1-8 = 1:1 | 0.83 | 10.023 | 0.61 | 5.14 |
| Example 11 | P3HT:Formula 1-1-9 = 1:1 | 0.56 | 9.79 | 0.48 | 2.66 |
| Example 12 | P3HT:Formula 1-1-10 = 1:1 | 0.59 | 9.82 | 0.50 | 2.95 |
| Comparative Example 1 | P3HT:PC$_{61}$BM = 1:1 | 0.66 | 10.04 | 0.46 | 3.10 |

Exemplary embodiments of the present invention have been described, but since the specific description is provided to inform a person with ordinary skill in the art to which the present invention belongs of the scope of the invention, it will be apparent that the range of the invention is not limited by the specific description. Accordingly, the substantial scope of the present invention will be defined by the appended claims and equivalents thereof.

The invention claimed is:

1. A fullerene derivative represented by the following Formula 1:

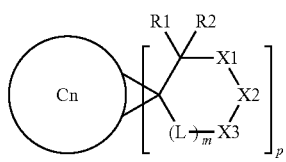

[Formula 1]

wherein:

Cn is a $C_{60}$ to $C_{84}$ fullerene;

p is an integer of 1 to 4, and when p is 2 or more, the structures in the parenthesis are the same as or different from each other;

L is CRaRb, and m is an integer of 0 to 3, and when m is 2 or more, Ls are the same as or different from each other;

X1 to X3 are the same as or different from each other, and are each independently S, O, PR, CRR', SO$_2$, P(=O)R, or SiRR', at least one of X1 to X3 is S, O, PR, SO$_2$, P(=O)R, or SiRR'; and R1, R2, Ra, Rb, R and R are the same as or different from each other, and are each independently hydrogen, deuterium, a halogen group, a nitrile group, a nitro group, an imide group, an amide group, a hydroxyl group, an ester group, a carbonyl group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group, or two substituents adjacent to each other in R1, R2, Ra, Rb, R and R' combine with each other to form a double bond, cycloalkyl, cycloalkenyl, cyclic ketone, or an aromatic ring, or two substituents in the same atom in R1, R2, Ra, Rb, R and R' combine with each other to form a spiro bond, a carbonyl group, an imine group, or an alkenyl group, the formed cycloalkyl, cycloalkenyl, aromatic ring, or spiro bond is unsubstituted or substituted with an additional substituent, when X1 and X3 are the same as or different from each other, and are each independently PR, CRR', P(=O)R, or SiRR', and m is 1, R1 or R2 and R or R' of X1, and Ra or Rb and R or R' of X3 do not form an aromatic ring simultaneously, and when X2 is S, m is 1, R1 and R2 are hydrogen, or Ra and Rb are hydrogen, and two substituents adjacent to each other in R1, R2, Ra, Rb, R and R' combine with each other to form an aromatic ring, the aromatic ring is substituted with an additional substituent.

2. The fullerene derivative of claim 1, wherein R1, R2, Ra, Rb, R and R' are the same as or different from each other, and are each independently hydrogen, a halogen group, an ester group, a substituted or unsubstituted alkyl group, a substituted or unsubstituted arylamine group, a substituted or unsubstituted alkoxy group, or a substituted or unsubstituted aryl group, or two substituents adjacent to each other in R1, R2, Ra, Rb, R and R' combine with each other to form a double bond, or an aromatic ring, or two substituents in the same atom in R1, R2, Ra, Rb, R and R' combine with each other to form a Spiro bond, or a carbonyl group, and the formed aromatic ring or spiro bond is unsubstituted or substituted with a halogen group, a substituted or unsubstituted alkoxy group, a substituted or unsubstituted alkyl group, or a substituted or unsubstituted arylamine group.

3. The fullerene derivative of claim 1, wherein m is 1.

4. The fullerene derivative of claim 1, wherein the structure in [ ] in Formula 1 is represented by any one of the following Formulae 2 to 10, 12 and 13:

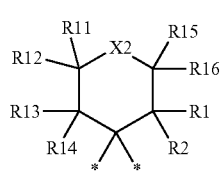

[Formula 2]

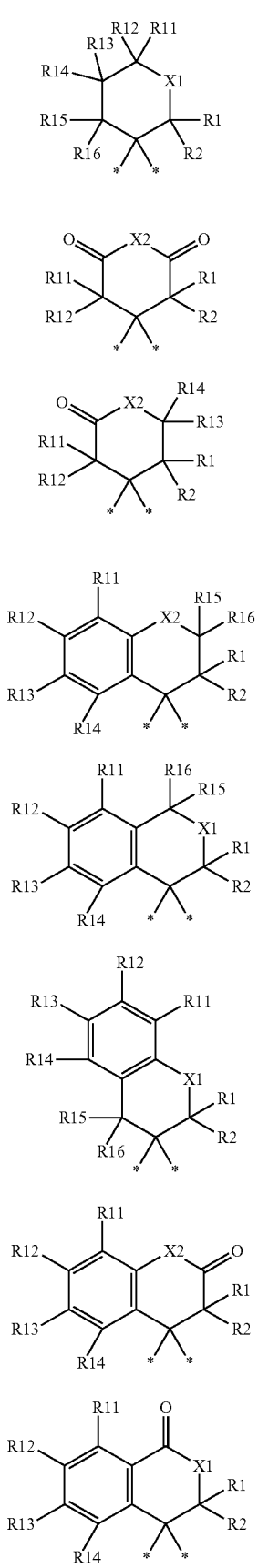

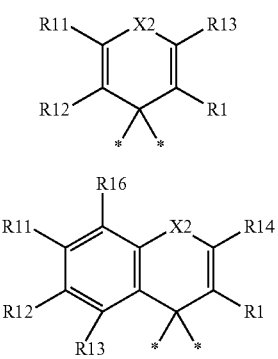

[Formula 12]

[Formula 13]

wherein:
X1, X2, R1 and R2 are the same as those defined in Formula 1;
R11 to R16 are the same as or different from each other, and are each independently hydrogen, deuterium, a halogen group, a nitrile group, a nitro group, an imide group, an amide group, a hydroxyl group, an ester group, a carbonyl group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, or a substituted or unsubstituted heterocyclic group, or two substituents adjacent to each other in R11 to R16 combine with each other to form a double bond, cycloalkyl, cycloalkenyl, cyclic ketone, or an aromatic ring, or two substituents in the same atom in R11 to R16 combine with each other to form a spiro bond, a carbonyl group, an imine group, or an alkenyl group, and the formed cycloalkyl, cycloalkenyl, cyclic ketone, aromatic ring, or spiro bond is unsubstituted or substituted with an additional substituent.

5. A fullerene derivative represented by the following Formula 1:

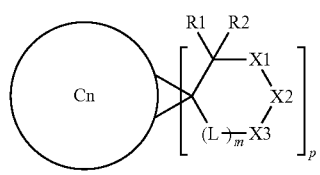

[Formula 1]

wherein:
$C_n$ is a $C_{60}$ to $C_{84}$ fullerene;
p is an integer of 1 to 4, and
when p is 2 or more, the structures in the parenthesis are the same as or different from each other; and
the structure in [ ] in Formula 1 is represented by any one of the following Formulae:

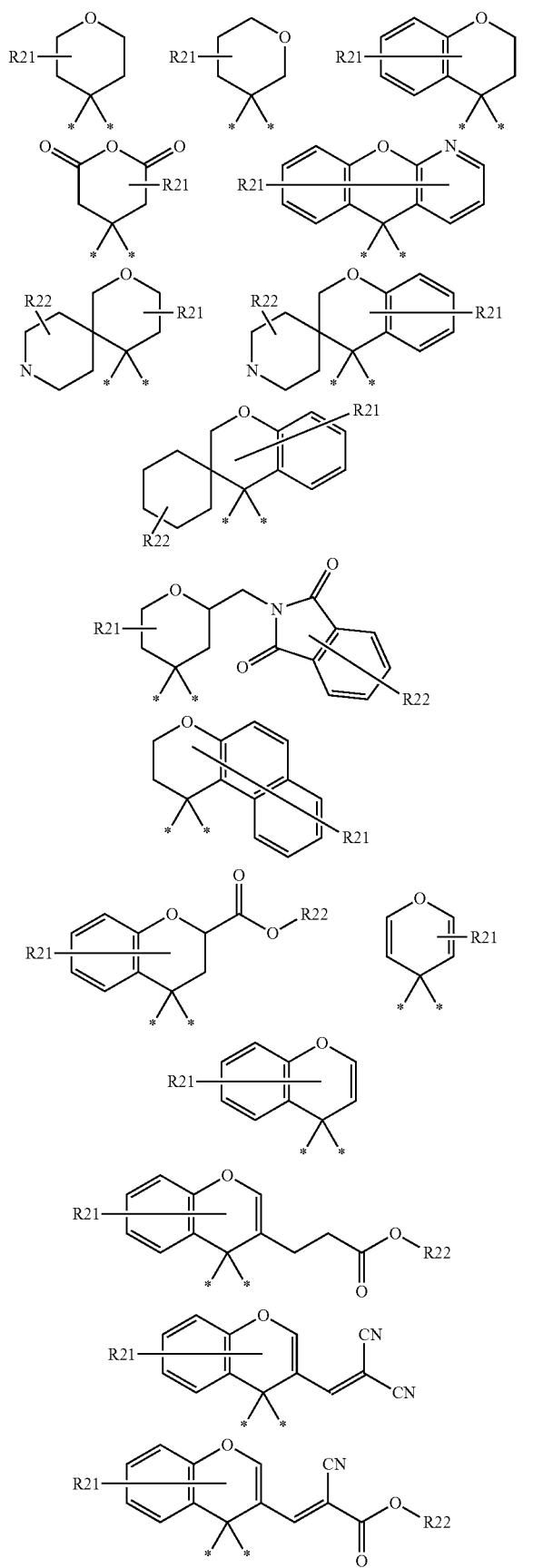

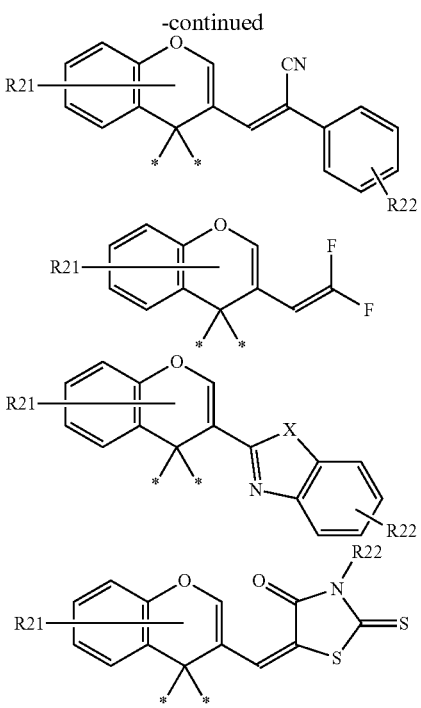

wherein:

X is S, O or NR23;

R21 is hydrogen, a halogen group, a substituted or unsubstituted alkyl group having 1 to 60 carbon atoms, a substituted or unsubstituted alkoxy group having 1 to 60 carbon atoms, a substituted or unsubstituted amine group having 1 to 60 carbon atoms, a substituted or unsubstituted aryl group having 6 to 60 carbon atoms, or a substituted or unsubstituted heterocyclic group having 2 to 60 carbon atoms; and R22 and R23 are the same as or different from each other, and are each independently hydrogen, a substituted or unsubstituted alkyl group having 1 to 60 carbon atoms, a substituted or unsubstituted aryl group having 6 to 60 carbon atoms, or a substituted or unsubstituted heterocyclic group having 2 to 60 carbon atoms.

6. A fullerene derivative represented by the following Formula 1:

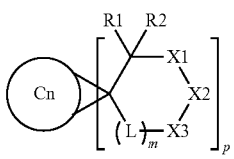

[Formula 1]

wherein:

$C_n$ is a $C_{60}$ to $C_{84}$ fullerene;

p is an integer of 1 to 4, and when p is 2 or more, the structures in the parenthesis are the same as or different from each other; and the structure in [ ] in Formula 1 is represented by any one of the following Formulae:

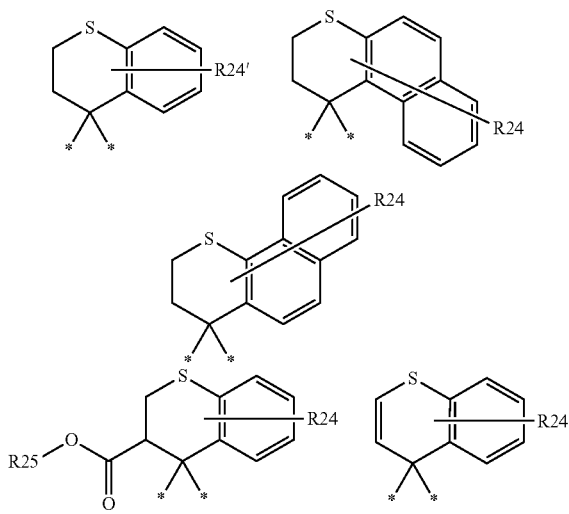

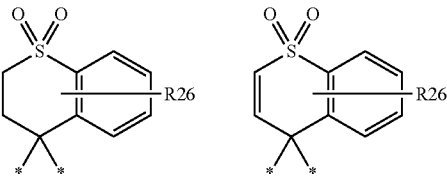

wherein:
R26 is hydrogen, a halogen group; a substituted or unsubstituted alkyl group having 1 to 60 carbon atoms, a substituted or unsubstituted alkoxy group having 1 to 60 carbon atoms, a substituted or unsubstituted amine group having 1 to 60 carbon atoms, a substituted or unsubstituted aryl group having 6 to 60 carbon atoms, or a substituted or unsubstituted heterocyclic group having 2 to 60 carbon atoms.

8. A fullerene derivative represented by the following Formula 1:

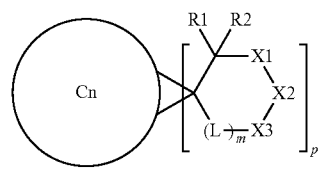

[Formula 1]

wherein:
Cn is a $C_{60}$ to $C_{84}$ fullerene;
p is an integer of 1 to 4, and
when p is 2 or more, the structures in the parenthesis are the same as or different from each other; and
the structure in [ ] in Formula 1 is represented by any one of the following Formulae:

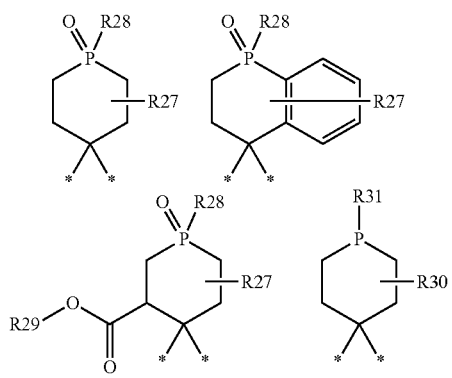

wherein:
R27 and R30 are the same as or different from each other, and are each independently hydrogen, a halogen group, a substituted or unsubstituted alkyl group having 1 to 60 carbon atoms, a substituted or unsubstituted alkoxy group having 1 to 60 carbon atoms, a substituted or unsubstituted amine group having 1 to 60 carbon atoms, a substituted or unsubstituted aryl group having 6 to 60 carbon atoms, or a substituted or unsubstituted heterocyclic group having 2 to 60 carbon atoms; and
R28, R29 and R31 are the same as or different from each other, and are each independently hydrogen, a substiwherein:
R24' is a halogen group, a substituted or unsubstituted alkyl group having 1 to 60 carbon atoms, a substituted or unsubstituted alkoxy group having 1 to 60 carbon atoms, a substituted or unsubstituted amine group having 1 to 60 carbon atoms, a substituted or unsubstituted aryl group having 6 to 60 carbon atoms, or a substituted or unsubstituted heterocyclic group having 2 to 60 carbon atoms;

R24 is hydrogen, a halogen group, a substituted or unsubstituted alkyl group having 1 to 60 carbon atoms, a substituted or unsubstituted alkoxy group having 1 to 60 carbon atoms, a substituted or unsubstituted amine group having 1 to 60 carbon atoms, a substituted or unsubstituted aryl group having 6 to 60 carbon atoms, or a substituted or unsubstituted heterocyclic group having 2 to 60 carbon atoms; and R25 is hydrogen, a substituted or unsubstituted alkyl group having 1 to 60 carbon atoms, an aryl group having 6 to 60 carbon atoms, or a substituted or unsubstituted heterocyclic group having 2 to 60 carbon atoms.

7. A fullerene derivative represented by the following Formula 1:

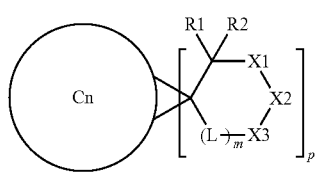

[Formula 1]

wherein:
Cn is a $C_{60}$ to $C_{84}$ fullerene;
p is an integer of 1 to 4, and
when p is 2 or more, the structures in the parenthesis are the same as or different from each other; and
the structure in [ ] in Formula 1 is represented by any one of the following Formulae:

tuted or unsubstituted alkyl group having 1 to 60 carbon atoms, a substituted or unsubstituted aryl group having 6 to 60 carbon atoms, or a substituted or unsubstituted heterocyclic group having 2 to 60 carbon atoms.

9. The fullerene derivative of claim 1, wherein the fullerene derivative has a LUMO energy level of −3.4 eV to −5.0 eV.

10. An organic solar cell comprising:
a first electrode;
a second electrode provided to face the first electrode; and
an organic material layer comprising one or more layers provided between the first electrode and the second electrode and including a photoactive layer,
wherein the one or more layers of the organic material layer comprise the fullerene derivative of claim 1.

11. The organic solar cell of claim 10, wherein the organic material layer comprises a hole transport layer, a hole injection layer, or a layer which transports and injects holes simultaneously, and
the hole transport layer, the hole injection layer, or the layer which transports and injects holes simultaneously comprises the fullerene derivative.

12. The organic solar cell of claim 10, wherein the organic material layer comprises an electron injection layer, an electron transport layer, or a layer which injects and transports electrons simultaneously, and
the electron injection layer, the electron transport layer, or the layer which injects and transports electrons simultaneously comprises the fullerene derivative.

13. The organic solar cell of claim 10, wherein the photoactive layer comprises one or two or more selected from the group consisting of an electron donor and an electron acceptor, and
the electron acceptor comprises the fullerene derivative.

14. The organic solar cell of claim 13, wherein the electron donor and the electron acceptor constitute a bulk heterojunction (BHJ).

15. The organic solar cell of claim 10, wherein the photoactive layer has a bilayer thin film structure comprising an n-type organic material layer and a p-type organic material layer, and
the n-type organic material layer comprises the fullerene derivative.

16. The organic solar cell of claim 10, wherein the organic solar cell further comprises one or two or more organic material layers selected from the group consisting of a hole injection layer, a hole transport layer, a hole blocking layer, a charge generation layer, an electron blocking layer, an electron injection layer, and an electron transport layer.

17. A method for fabricating an organic solar cell, the method comprising:
preparing a substrate;
forming a first electrode on an upper portion of the substrate;
forming an organic material layer comprising one or more layers, which comprises a photoactive layer on an upper portion of the first electrode; and
forming a second electrode on an upper portion of the organic material layer,
wherein the one or more layers of the organic material layer comprise the fullerene derivative of claim 1.

18. An organic solar cell comprising:
a first electrode;
a second electrode provided to face the first electrode; and
an organic material layer comprising one or more layers provided between the first electrode and the second electrode and including a photoactive layer,
wherein the one or more layers of the organic material layer comprise the fullerene derivative of claim 5.

19. An organic solar cell comprising:
a first electrode;
a second electrode provided to face the first electrode; and
an organic material layer comprising one or more layers provided between the first electrode and the second electrode and including a photoactive layer,
wherein the one or more layers of the organic material layer comprise the fullerene derivative of claim 6.

20. An organic solar cell comprising:
a first electrode;
a second electrode provided to face the first electrode; and
an organic material layer comprising one or more layers provided between the first electrode and the second electrode and including a photoactive layer,
wherein the one or more layers of the organic material layer comprise the fullerene derivative of claim 7.

21. An organic solar cell comprising:
a first electrode;
a second electrode provided to face the first electrode; and
an organic material layer comprising one or more layers provided between the first electrode and the second electrode and including a photoactive layer,
wherein the one or more layers of the organic material layer comprise the fullerene derivative of claim 8.

* * * * *

UNITED STATES PATENT AND TRADEMARK OFFICE
CERTIFICATE OF CORRECTION

PATENT NO. : 10,270,038 B2
APPLICATION NO. : 15/112056
DATED : April 23, 2019
INVENTOR(S) : Bae et al.

Page 1 of 1

It is certified that error appears in the above-identified patent and that said Letters Patent is hereby corrected as shown below:

In the Claims

Column 47, Line 60, Claim 1: Please correct "R and R" to read -- R and R' --

Column 48, Line 47, Claim 2: Please correct "Spiro" to read -- spiro --

Signed and Sealed this
Twenty-seventh Day of August, 2019

Andrei Iancu
*Director of the United States Patent and Trademark Office*